(12) United States Patent
Kimura

(10) Patent No.: US 9,044,483 B2
(45) Date of Patent: Jun. 2, 2015

(54) CELL DEATH INHIBITION BY MACROPHAGE MIGRATION INHIBITORY FACTOR AND A BINDING SUBSTANCE THERETO

(75) Inventor: Haruhide Kimura, Osaka (JP)

(73) Assignee: Takeda Pharmaceuticals Company Limited, Osaka (JP)

( * ) Notice: Subject to any disclaimer, the term of this patent is extended or adjusted under 35 U.S.C. 154(b) by 579 days.

(21) Appl. No.: 12/442,091

(22) PCT Filed: Sep. 21, 2007

(86) PCT No.: PCT/JP2007/069141
§ 371 (c)(1),
(2), (4) Date: Mar. 19, 2009

(87) PCT Pub. No.: WO2008/035823
PCT Pub. Date: Mar. 27, 2008

(65) Prior Publication Data
US 2009/0270326 A1    Oct. 29, 2009

(30) Foreign Application Priority Data
Sep. 22, 2006  (JP) ................................ 2006-257487

(51) Int. Cl.
 C07K 14/52    (2006.01)
 C07D 279/04   (2006.01)
 A61K 31/5415  (2006.01)
 A61K 38/19    (2006.01)

(52) U.S. Cl.
 CPC ............. *A61K 31/5415* (2013.01); *A61K 38/19* (2013.01)

(58) Field of Classification Search
None
See application file for complete search history.

(56) References Cited

FOREIGN PATENT DOCUMENTS

| EP | 1 500 402 | * | 1/2005 |
|----|-----------|---|--------|
| EP | 1568697 A1 | * | 8/2005 |
| JP | 2004-002404 | | 1/2004 |
| JP | 2004-196792 | | 7/2004 |
| WO | WO-02/18356 | | 3/2002 |
| WO | WO-03/020719 | | 3/2003 |
| WO | WO-03/090782 | | 11/2003 |
| WO | WO-2006/132438 | | 12/2006 |

OTHER PUBLICATIONS

Senter et al., Inhibition of macrophage migration inhibitory factor (MIF) tautomerase and biological activities by acetaminophen metabolites, Proc. Nat. Acad. Sci, USA, 90(1):144-149, Jan. 8, 2002.*

Morand et al., MIF: a new cytokine link between rheumatoid arthritis and atherosclerosis, Nat. Rev. Drug Discov. pp. 1-12 Advanced Online Publication, published online Apr. 13, 2006.*

Ren et al., Inhibition of tumor growth and metastasis in vitro and in vivo targeting macrophage migration inhibitory factor in human neuroblastoma, Oncogene, 25:3501-3508, 2006.*

(Continued)

*Primary Examiner* — Claire Kaufman
(74) *Attorney, Agent, or Firm* — Mintz Levin Cohn Ferris Glovsky and Popeo, P.C.; David Conlin, Esq.

(57) ABSTRACT

The present invention relates to an antioxidant response element (ARE) activator comprising a macrophage migration inhibitory factor (MIF) or a modified form thereof, an ARE activator comprising a combination of MIF or a modified form thereof and a substance capable of binding to MIF, such as a 1,3-benzothiazinone, and so on. These ARE activators are useful.

6 Claims, 6 Drawing Sheets

(56) References Cited

OTHER PUBLICATIONS

Calandra et al., Protection from septic shock by neutralization of macrophage migration inhibitory factor, Nature Med. 6(2):164-170, Feb. 2000.*

Bozza et al. Targeted disruption of migration inhibitory factor gene reveals its critical role in sepsis, J. Exp. Med. 189(2): 341-346, Jan. 1999.*

Jaiswal, AK, Regulation of genes encoding NAD(P)H:quinone oxidoreductases, Free Radical Biol. Med. 29(3/4):254-262, 2000.*

Li et al., Preventative effect of erythropoietin on cardiac dysfunction in doxorubicin-induced cardiomyophaty, Circulation, 113:535-543, 2006.*

Garner et al., Macrophage migration inhibitory factor is a cardiac-derived myocardial depressant factor, Am. J. Pysiol. Heart Cir. Physiol. 285(6):H2500-2509, 2003.*

Chagnon et al., Endotoxin-induced myocardial dysfunction: Effects of macrophage migration inhibitory factor neutralization, Circ Res. 96:1095-1102, 2005.*

International Search Report issed in International Application No. PCT/JP2007/069141, Nov. 13, 2007.

Hudson, et al., "A proinflammatory cytokine inhibits p53 tumor suppressor activity", J Exp Med, 1999, vol. 190. No. 10, p. 1375-82.

Lolis et al., "Macrophage migration inhibitory factor", Expert Opin. Ther. Targets, 7, 153-164 (2003).

Mitchell, et al., "Macrophage migration inhibitory factor (MIF) sustains macrophage proinflammatory function by inhibiting p53: regulatory role in the innate immune response", Proc Natl Acad Sci USA, 2002, vol. 99, No. 1, p. 345-50.

Nguyen et al., "The Cytokine Macrophage Migration Inhibitory Factor Reduces Pro-Oxidative Stress-Induced Apoptosis", J. Immunol. 170, 3337-3347 (2003).

Takahashi et al., "Macrophage migration inhibitory factor as a redox-sensitive cytokine in cardiac myocytes" Cardiovascular Res., 52, 438-445 (2001).

Nonaka, Yukari "Macrophage Yuso Soshi Inshi (MIF) ni yoru NO Yudosei Saiboshi no Yokusei", Japan Society for Bioscience, Biotechnology, and Agrochemistry 2003 Nendo (Heisei 15 Nendo) Taikai Koen Yoshishu, Mar. 5, 2003, p. 144.

Morand E F, et al. "Macrophage migration inhibitory factor in rheumatoid arthritis." Front Biosci. Jan. 1, 2005;10:12-22.

Thiele M, et al. "Link between macrophage migration inhibitory factor and cellular redox regulation." Antioxid Redox Signal. Sep.-Oct. 2005;7(9-10):1234-48.

Supplemental European Search Report for European Application No. EP07828882, completed Jun. 7, 2011 Jun. 24, 2011.

* cited by examiner

SEQUENCE LISTING

<160> NUMBER OF SEQ ID NOS: 21

<210> SEQ ID NO 1
<211> LENGTH: 114
<212> TYPE: PRT
<213> ORGANISM: Homo sapiens

<400> SEQUENCE: 1

Pro Met Phe Ile Val Asn Thr Asn Val Pro Arg Ala Ser Val Pro Asp
1               5                   10                  15
Gly Phe Leu Ser Glu Leu Thr Gln Gln Leu Ala Gln Ala Thr Gly Lys
            20                  25                  30
Pro Pro Gln Tyr Ile Ala Val His Val Val Pro Asp Gln Leu Met Ala
        35                  40                  45
Phe Gly Gly Ser Ser Glu Pro Cys Ala Leu Cys Ser Leu His Ser Ile
    50                  55                  60
Gly Lys Ile Gly Gly Ala Gln Asn Arg Ser Tyr Ser Lys Leu Leu Cys
65                  70                  75                  80
Gly Leu Leu Ala Glu Arg Leu Arg Ile Ser Pro Asp Arg Val Tyr Ile
                85                  90                  95
Asn Tyr Tyr Asp Met Asn Ala Ala Asn Val Gly Trp Asn Asn Ser Thr
            100                 105                 110
Phe Ala

<210> SEQ ID NO 2
<211> LENGTH: 39
<212> TYPE: DNA
<213> ORGANISM: Artificial Sequence
<220> FEATURE:
<223> OTHER INFORMATION: Primer

<400> SEQUENCE: 2
gaagaagctc ttccgcaggc gaaggtggag ttgttccag                              39

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
gatatacata tgtcgatgtt catcg                                             25

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
cgatgaacat cgacatatgt atatc                                             25

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5

```
ccatatgccg atgttcatcg taaacac                                         27
```

<210> SEQ ID NO 6
<211> LENGTH: 42
<212> TYPE: DNA
<213> ORGANISM: Rat

<400> SEQUENCE: 6

```
gagcttggaa atggcattgc taatggtgac aaagcaactt tg                       42
```

<210> SEQ ID NO 7
<211> LENGTH: 114
<212> TYPE: PRT
<213> ORGANISM: Rattus norvegicus

<400> SEQUENCE: 7

```
Pro Met Phe Ile Val Asn Thr Asn Val Pro Arg Ala Ser Val Pro Glu
                  5                  10                  15
Gly Phe Leu Ser Glu Leu Thr Gln Gln Leu Ala Gln Ala Thr Gly Lys
             20                  25                  30
Pro Ala Gln Tyr Ile Ala Val His Val Val Pro Asp Gln Leu Met Thr
         35                  40                  45
Phe Ser Gly Thr Ser Asp Pro Cys Ala Leu Cys Ser Leu His Ser Ile
     50                  55                  60
Gly Lys Ile Gly Gly Ala Gln Asn Arg Asn Tyr Ser Lys Leu Leu Cys
 65                  70                  75                  80
Gly Leu Leu Ser Asp Arg Leu His Ile Ser Pro Asp Arg Val Tyr Ile
                 85                  90                  95
Asn Tyr Tyr Asp Met Asn Ala Ala Asn Val Gly Trp Asn Asn Ser Thr
                100                 105                 110
Phe Ala
```

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8

```
gatgatcata tgcctatgtt catcgtgaac                                      30
```

<210> SEQ ID NO 9
<211> LENGTH: 39
<212> TYPE: DNA
<213> ORGANISM: Artificial Sequence
<220> FEATURE:
<223> OTHER INFORMATION: Primer

<400> SEQUENCE: 9

```
gaagaagctc ttccgcaagc gaaggtggaa ccgttccag                            39
```

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10

```
cggaattcat catgccgatg ttcatcgt                                        28
```

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
gcctcgagtt aggcgaaggt ggagttgt                                        28

<210> SEQ ID NO 12
<211> LENGTH: 30
<212> TYPE: PRT
<213> ORGANISM: Artificial
<220> FEATURE:
<223> OTHER INFORMATION: Added peptide sequence with histidin tag

<400> SEQUENCE: 12

Met His His His His His His Ser Ser Gly Leu Val Pro Arg Gly Ser
1               5                   10                  15

Gly Met Lys Glu Thr Ala Ala Ala Lys Phe Glu Phe Ile Met
            20                  25                  30

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
tgccagcctt ctgacctctt t                                               21

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
ctgcaggaac ttcttcacat tgg                                             23

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
aaggccttca agagcagaat cagcagc                                         27

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
tgccaagtat gatgacatca agaag                                           25

<210> SEQ ID NO 17
<211> LENGTH: 20

```
<212> TYPE: DNA
<213> ORGANISM: Artificial Sequence
<220> FEATURE:
<223> OTHER INFORMATION: Primer

<400> SEQUENCE: 17
agcccaggat gccctttagt                                              20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tggtgaagca ggcggccgag                                              20

<210> SEQ ID NO 19
<211> LENGTH: 18
<212> TYPE: DNA
<213> ORGANISM: Artificial Sequence
<220> FEATURE:
<223> OTHER INFORMATION: Primer

<400> SEQUENCE: 19
ccgccttcct gctcaaca                                                18

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
aagaaactct gtctgtgagg gactct                                       26

<210> SEQ ID NO 21
<211> LENGTH: 28
<212> TYPE: DNA
<213> ORGANISM: Artificial Sequence
<220> FEATURE:
<223> OTHER INFORMATION: Primer

<400> SEQUENCE: 21
caggcactgc tgacagagga acacaaag                                     28
```

CELL DEATH INHIBITION BY MACROPHAGE MIGRATION INHIBITORY FACTOR AND A BINDING SUBSTANCE THERETO

This application is the U.S. National Phase application, pursuant to 35 U.S.C. §371, of PCT International Application Ser. No. PCT/JP2007/069141, filed Sep. 21, 2007, published as WO 2008/035823, which claims the benefit of Japanese Application No. 2006-257487, filed Sep. 22, 2006; the entire contents of each of which are incorporated herein by reference in their entirety.

TECHNICAL FIELD

The present invention relates to a cell death inhibitor, an antioxidant response element (ARE) activator, and the like.

BACKGROUND ART

Heretofore, macrophage migration inhibitory factor (MIF) is thought to be an exacerbation factor of various inflammatory diseases, which is released from immunocompetent cells, pituitary, etc. in rapid response to stimuli including body invasion and is located upstream of the inflammatory cytokine cascade to control inflammatory responses (Annual Reports in Medicinal Chemistry, 33, 24, 1998; Advances in Immunology, 66, 197, 1997).

MIF levels markedly increase in the synovial fluid or serum from the patient with rheumatism, in the alveolar lavage fluid from the patient with acute respiratory distress syndrome, in the urine collected during rejection from the patient who has received a kidney transplant and in the serum from the patient with acute myocardial infarction, diabetes mellitus, systemic lupus erythematosus, Crohn's disease and atopic dermatitis, as compared to healthy individuals.

It is reported that administration of an antibody against MIF and loss of MIF in various animal disease models show improving effects on symptoms of nephritis, hepatitis, pneumonia, arthritis, endotoxin shock, etc. (International Journal of Molecular Medicine, 2, 17, 1998).

In recent years, it is reported that MIF suppresses cell death induced by oxidative stress (J. Exp. Med., 190, 1375-1382, 1999 PNAS, 99, 345-350, 2001) and induces GST expression (Cardiovascular Res., 52, 438-445, 2001). 1,3-Benzothiazinone derivatives having a cell death inhibitory activity and capable of binding to MIF are reported in WO 03/20719 (Patent Document 1). It is described in WO 03/90782 that substances capable of binding to MIF (e.g., 1,3-benzothiazinone derivatives) potentiate the cell death inhibitory activity and the expression of a gene or protein production under control of antioxidant response element (ARE).

It is reported that by kinetic analysis, the Pro at the position-1 in MIF forms a hydrophobic pocket with Lys-32, Ile-64, Tyr-95 and Asn-97 to bind to various compounds (Expert Opin. Ther. Targets, 7, 153-164, 2003).

On the other hand, it has been revealed in recent years that cell death induced by oxidative stress is deeply correlated with occurring and developing of numerous disorders including neurodegenerative diseases (e.g., Alzheimer's disease, Parkinson's disease, amyotrophic lateral sclerosis, etc.), ischemic diseases (e.g., myocardial infarction, heart failure, apoplexy, cerebral infarction, ischemic acute renal failure, etc.), bone/joint diseases (e.g., osteoporosis, degenerative arthritis, rheumatism, etc.), digestive diseases (e.g., inflammatory bowel disorders, acute pancreatitis, etc.), hepatic diseases (e.g., alcoholic hepatitis, viral hepatitis, etc.), diabetes mellitus, AIDS, etc. (Extra Issue: Igaku-no-Ayumi, page 79, 2005; Extra Issue: Igaku-no-Ayumi, page 8, 1997; Nippon Rinsho, 54, 1996). The antioxidant response element (ARE) regulates the expression of a variety of protective factors against oxidative stress and its transcriptional activation is considered as one of the most important cytoprotective mechanisms against oxidative stress (Current Pharmaceutical Design, 10, 879, 2004). Furthermore, it is pointed out the possibility that overexpression of protective factors regulated by ARE would be associated with pharmaceutical effects of gold preparations and NSAIDs used for the treatment of rheumatoid arthritis (The Journal of Biological Chemistry, 276, 34074, 2001; Free Radical Biology and Medicine, 37, 650, 2002).

DISCLOSURE OF INVENTION

Based on the foregoing, it is expected that ARE activation would result in suppression of oxidative stress-associated diseases. It is eagerly demanded, therefore, to develop a safe and potent cell death inhibitor having an ARE activation as the major action.

In view of the foregoing situation, the present inventors have made extensive investigations and as a result, found that a) 1,3-benzothiazinone derivatives capable of specifically binding to MIF binds in the vicinity of the N terminus of MIF, b) MIF activates ARE in the presence of the derivative capable of binding to MIF, c) MIF activates ARE, etc. Based on these findings, the inventors have conducted further studies and come to accomplish the present invention.

More specifically, the present invention relates to the following features, and so on.

[1] An ARE activator (or composition) comprising MIF or a modified form thereof.

[2] The activator according to [1] above, wherein the MIF is a protein comprising the amino acid sequence represented by SEQ ID NO: 1 or SEQ ID NO: 7, or a salt thereof.

[2a] The activator according to [1] above, wherein the modified MIF is a modified protein comprising substantially the same amino acid sequence represented by SEQ ID NO: 1, or a salt thereof.

[2b] The activator according to [1] above, wherein the modified MIF is a modified protein comprising the amino acid sequence having at least 95% homology to the amino acid sequence represented by SEQ ID NO: 1, or a salt thereof, and having an ARE activation action or/and a cell death inhibitory activity.

[2c] The activator according to [1] above, wherein the modified MIF is a modified protein comprising the amino acid sequence, in which one to several (e.g., 1 to 6) amino acid(s) is/are deleted, substituted and/or added, in the amino acid sequence represented by SEQ ID NO: 1, or a salt thereof, and having an ARE activation activity and/or a cell death inhibitory activity.

[3] The activator according to [1] above, wherein the modified MIF is a modified protein in which at least one amino acid selected from the amino acids in the vicinity of N-terminal side and positions 32 (e.g., 22 to 42, preferably 27 to 37, more preferably 30 to 34), 64 (e.g., 54 to 74, preferably 59 to 69, more preferably 62 to 66), 95 (e.g., 85 to 96, preferably 90 to 96, more preferably 93 to 96) and 97 (e.g., 97 to 107, preferably 97 to 102, more preferably 97 to 99) of the amino acid sequence represented by SEQ ID NO: 1 is deleted, added or/and substituted.

[4] The activator according to [3] above, wherein the N-terminal side is a sequence of amino acids 1 to 5 in the amino acid sequence represented by SEQ ID NO: 1.

[5] An ARE activator comprising a combination of a MIF or a modified form thereof and a substance capable of binding to the MIF.

[5a] The activator according to [5] above, wherein the substance is an anti-MIF antibody.

[6] The activator according to [5] above, wherein the substance is a substance capable of activating the MIF.

[7] The activator according to [5] above, wherein the substance is a 1,3-benzothiazinone derivative.

[8] The activator according to [7] above, wherein the 1,3-benzothiazinone derivative is a compound represented by formula:

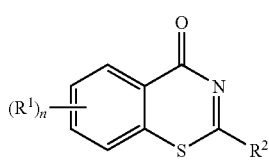

wherein $R^1$ represents hydrogen atom, a halogen atom, hydroxy, nitro, an alkyl which may optionally be halogenated, an alkoxy which may optionally be substituted, an acyl or an amino which may optionally be substituted;

$R^2$ represents a hydrocarbon group which may optionally be substituted, an aromatic heterocyclic group which may optionally be substituted, or an amino which may optionally be substituted; and, n represents 1 or 2; or
a salt thereof.

[9] A cell death inhibitor comprising a modified MIF.

[10] The inhibitor according to [9] above, wherein the MIF is a protein comprising the amino acid sequence represented by SEQ ID NO: 1 or SEQ ID NO: 7.

[10a] The inhibitor according to [9] above, wherein the modified MIF is a modified protein comprising substantially the same amino acid sequence represented by SEQ ID NO: 1, or a salt thereof.

[10b] The inhibitor according to [9] above, wherein the modified MIF is a modified protein comprising the amino acid sequence having at least 95% homology to the amino acid sequence represented by SEQ ID NO: 1, or a salt thereof, and having an ARE activation activity or/and a cell death inhibitory activity.

[10c] The inhibitor according to [9] above, wherein the modified MIF is a modified protein comprising the amino acid sequence, in which one to several (e.g., 1 to 6) amino acid(s) is/are deleted, substituted and/or added, in the amino acid sequence represented by SEQ ID NO: 1, or a salt thereof, and having an ARE activation activity and/or a cell death inhibitory activity.

[11] The inhibitor according to [9] above, wherein the modified MIF is a modified protein in which at least one amino acid selected from the amino acids in the vicinity of N-terminal side and positions 32 (e.g., 22 to 42, preferably 27 to 37, more preferably 30 to 34), 64 (e.g., 54 to 74, preferably 59 to 69, more preferably 62 to 66), 95 (e.g., 85 to 96, preferably 90 to 96, more preferably 93 to 96) and 97 (e.g., 97 to 107, preferably 97 to 102, more preferably 97 to 99) of the amino acid sequence represented by SEQ ID NO: 1 is deleted, added or/and substituted.

[12] The inhibitor according to [11] above, wherein the N-terminal side is a sequence of amino acids 1 to 5 in the amino acid sequence represented by SEQ ID NO: 1.

[13] A cell death inhibitor comprising a combination of MIF or a modified form thereof and a substance capable of binding to the MIF.

[14] The inhibitor according to [13] above, wherein the substance is a substance capable of activating the macrophage migration inhibitory factor.

[15] The inhibitor according to [13] above, wherein the substance is a 1,3-benzothiazinone derivative.

[16] The inhibitor according to [15] above, wherein the 1,3-benzothiazinone derivative is a compound represented by formula:

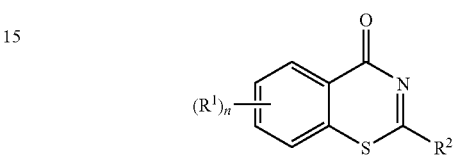

wherein $R^1$ represents hydrogen atom, a halogen atom, hydroxy, nitro, an alkyl which may optionally be halogenated, an alkoxy which may optionally be substituted, an acyl or an amino which may optionally be substituted;

$R^2$ represents a hydrocarbon group which may optionally be substituted, an aromatic heterocyclic group which may optionally be substituted, or an amino which may optionally be substituted; and, n represents 1 or 2; or
a salt thereof.

[17] The activator or inhibitor according to any one of [1] through [16] above, which is an agent for the prevention/treatment of a cardiovascular disease, a bone/joint disease, an infectious disease, an inflammatory disease, a renal disease, a central nervous system disease, cancer or diabetes.

[18] A method of activating an ARE which comprises modifying MIF.

[19] A method of suppressing cell death which comprises modifying MIF.

[20] A method of preventing/treating a cardiovascular disease, a bone/joint disease, an infectious disease, an inflammatory disease, a renal disease, a central nervous system disease, cancer or diabetes, which comprises modifying a MIF.

[21] A method of preventing/treating a cardiovascular disease, a bone/joint disease, an infectious disease, an inflammatory disease, a renal disease, a central nervous system disease, cancer or diabetes, which comprises a combination of a macrophage migration inhibitory factor or a modified form thereof and a substance capable of binding to the macrophage migration inhibitory factor.

[22] Use of a macrophage migration inhibitory factor or a modified form thereof to produce an antioxidant response element activator.

[23] Use of a macrophage migration inhibitory factor or a modified form thereof in combination with a substance capable of binding to the macrophage migration inhibitory factor to produce an antioxidant response element activator.

[24] Use of a modified macrophage migration inhibitory factor to produce a cell death inhibitor.

[25] Use of a macrophage migration inhibitory factor or a modified form thereof and a substance capable of binding to the macrophage migration inhibitory factor to produce a cell death inhibitor.

[26] Use of a macrophage migration inhibitory factor or a modified form thereof to produce a medicament for preventing/treating a cardiovascular disease, a bone/joint disease, an infectious disease, an inflammatory disease, a renal disease, a central nervous system disease, cancer or diabetes.

[27] Use of a macrophage migration inhibitory factor or a modified form thereof and a substance capable of binding to the macrophage migration inhibitory factor to produce a medicament for preventing/treating a cardiovascular disease, a bone/joint disease, an infectious disease, an inflammatory disease, a renal disease, a central nervous system disease, cancer or diabetes.

(a) MIF or its modified form is useful as the ARE activator, and (b) the combination of MIF or its modified form and the substance capable of binding to MIF (e.g., the 1,3-benzothiazinone derivative, antibody, etc.) as the ARE activator are useful as safe and excellent cell death inhibitors, for example, as agents for the prevention/treatment of cardiovascular diseases, bone/joint diseases, infectious diseases, inflammatory diseases, renal diseases, central nervous system diseases, cancer, diabetes, etc.

Figure 1:
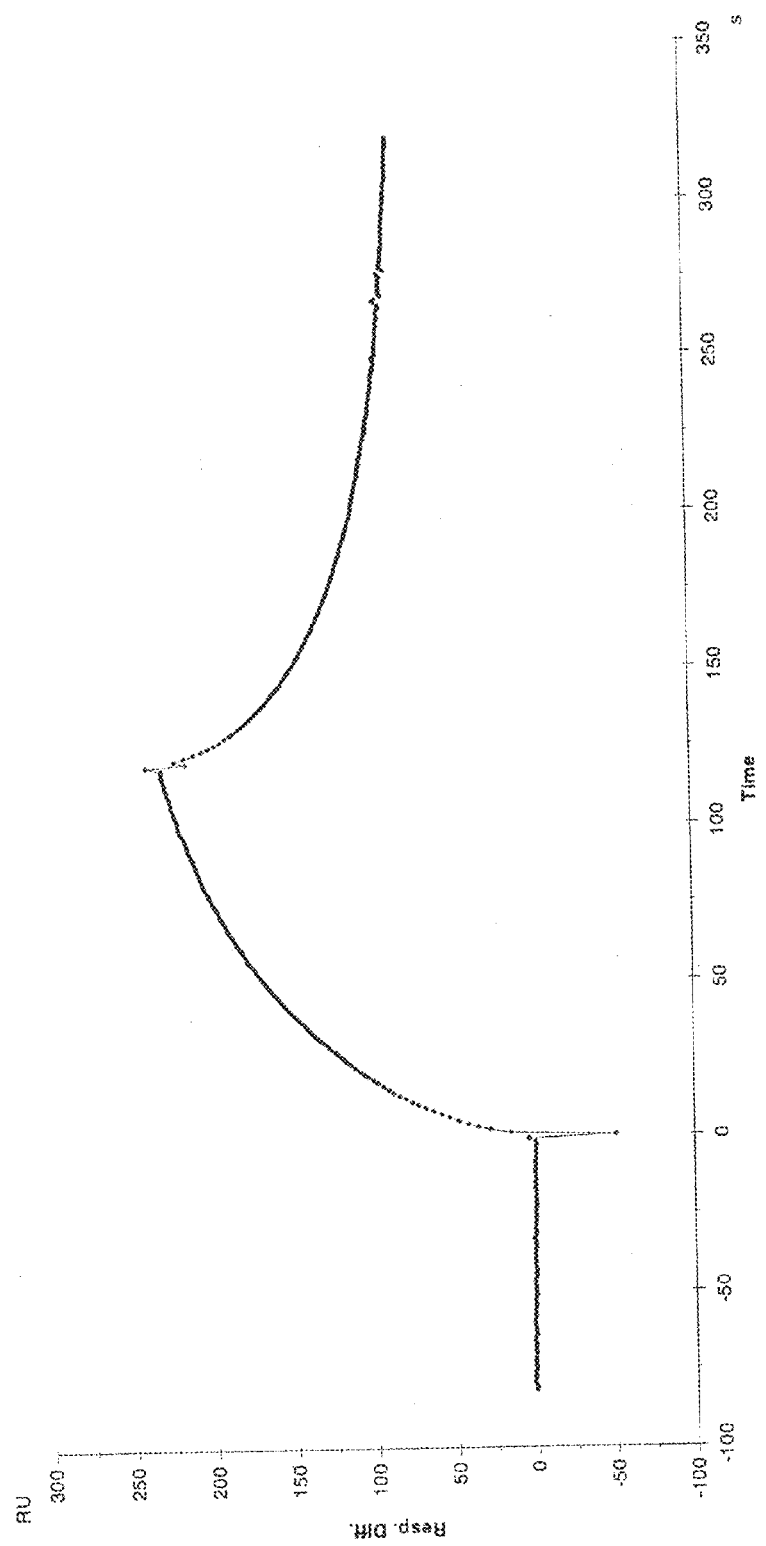
FIG. 1 shows the results of binding between rat MIF and Compound A, wherein the ordinate represents the surface plasmon resonance signals (resonance units) and the abscissa represents time (seconds).

1. MIF or its Modified Form Used in the Present Invention

The macrophage migration inhibitory factor (MIF) used in the present invention includes the protein comprising the amino acid sequence represented by SEQ ID NO: 1 (hMIF) or SEQ ID NO: 7 (rMIF), or salts thereof, etc. The modified form of MIF includes the protein comprising such an amino acid sequence that is substantially the same as the amino acid sequence represented by SEQ ID NO: 1 or SEQ ID NO: 7, or salts thereof, etc. The protein comprising the amino acid sequence that is substantially the same as the amino acid sequence represented by SEQ ID NO: 1 or SEQ ID NO: 7 includes proteins comprising amino acid sequences having homology of at least about 50%, preferably at least 70%, preferably at least 80%, preferably at least 90%, and preferably at least 95%, to the amino acid sequence represented by SEQ ID NO: 1 or SEQ ID NO: 7, and having the same physiological activities (ARE activation activity or/and cell death inhibitory activity) as in MIF.

The protein comprising substantially the same amino acid sequence as the amino acid sequence represented by SEQ ID NO: 1 or SEQ ID NO: 7 includes proteins wherein 1 or at least 2 (preferably approximately 1 to 20, more preferably approximately 1 to 10 and most preferably approximately several (1 to 5)) amino acids may be deleted of the amino acid sequence, 1 or at least 2 (preferably approximately 1 to 20, more preferably approximately 1 to 10 and most preferably approximately several (1 to 6)) amino acids may be added to in the amino acid sequence, 1 or at least 2 (preferably approximately 1 to 20, more preferably approximately 1 to 10 and most preferably approximately several (1 to 6)) amino acids may be inserted into the amino acid sequence, or, 1 or at least 2 (preferably approximately 1 to 20, more preferably approximately 1 to 10 and most preferably approximately several (1 to 6)) amino acids in the amino acid sequence may be substituted with other amino acid(s), and have the same physiological activities (ARE activation activity or/and cell death inhibitory activity) as those of MIF.

The modified MIF includes, for example, variants wherein at least one amino acid (e.g., 1 to 10, preferably 1 to 5 and more preferably 1 or 2 amino acids) selected from the amino acids in the vicinity of N-terminal side (e.g., a sequence of amino acids 1 to 5) and positions 32 (e.g., 22 to 42, more preferably 27 to 37 and most preferably 30 to 34), 64 (e.g., 54 to 74, more preferably 59 to 69 and most preferably 62 to 66), 95 (e.g., 85 to 96, more preferably 90 to 96 and most preferably 93 to 96) and 97 (e.g., 97 to 107, more preferably 97 to 102 and most preferably 97 to 99) in the amino acid sequence represented by SEQ ID NO: 1 is/are deleted, added or/and substituted. It is reported that a substance binding to MIF binds in the vicinity of the N terminus (Pro) of MIF, MIF activates ARE in the presence of the substance capable of binding to MIF, and the Pro at the position-1 in MIF forms a hydrophobic pocket with Lys-32, Ile-64, Tyr-95 and Asn-97 to bind to various compounds (Expert Opin. Ther. Targets, 7, 153-164, 2003). It is thus considered that the amino acids in the vicinity of N-terminal side and positions 32, 64, 95 and 97 in the amino acid sequence represented by SEQ ID NO: 1 are closely related to ARE activation. Accordingly, it is considered that the modified MIF wherein at least one amino acid from the amino acids described above is deleted, added or/and substituted could have significant ARE activation and cell death inhibitory activities.

The following amino acid residues in the same group are mutually substitutable in general, though the amino acid is not limited thereto.

Group 1: leucine, isoleucine, norleucine, valine, norvaline, alanine, 2-aminobutanoic acid, methionine, o-methylserine, t-butylglycine, t-butylalanine and cyclohexylalanine Group 2: aspartic acid, glutamic acid, isoaspartic acid, isoglutamic acid, 2-aminoadipic acid and 2-aminosuberic acid Group 3: asparagine and glutamine Group 4: lysine, arginine, ornithine, 2,4-diaminobutanoic acid and 2,3-diaminopropionic acid Group 5: proline, 3-hydroxyproline and 4-hydroxyproline Group 6: serine, threonine and homoserine Group 7: phenylalanine and tyrosine Accordingly, the modified MIF wherein the amino acids in the vicinity of N-terminal side, amino acids 32, 64, 95 and 97 of the amino acid sequence represented by SEQ ID NO: 1 is substituted with the substitutable amino acid(s) listed in Groups 1 through 7 described above can be preferably used in the present invention.

In the modified MIF which can be used in the present invention, amino acids other than those in the vicinity of N-terminal side, amino acids 32, 64, 95 and 97 of the amino acid sequence represented by SEQ ID NO: 1 can also be modified, so long as the modified form has a desired pharmacological activity (ARE activation activity or/and cell death inhibitory activity). Such a modified MIF includes, for example, proteins having comprising amino acid sequences wherein one or more (e.g., 1 to 10, preferably 1 to several (e.g., 1 to 6) and more preferably 1 or 2) amino acids are deleted, substituted, added and/or inserted in the sequence part other than the amino acids in the vicinity of N-terminal side, amino acids 32, 64, 95 and 97 of the amino acid sequence represented by SEQ ID NO: 1.

The modified MIF further includes MIF in which a substance capable specifically to MIF (e.g., a 1,3-benzothiazinone derivative, an anti-MIF antibody, etc.) is bound to MIF, and the like.

The MIF and its modified form may be those commercially available, or can be prepared by methods publicly known or their modifications. The MIF and its modified form which can be used in the present invention can also be prepared by, for example, known genetic engineering techniques (cf., e.g., the procedures described in EXAMPLES, REFERENCE EXAMPLES, EXPERIMENTS, etc. later described), known methods for protein/peptide synthesis, etc. These known methods for protein/peptide synthesis include, for example, solid synthesis, liquid synthesis, etc. (see (i) M. Bodanszky and M. A. Ondetti, Peptide Synthesis, Interscience Publishers, New York (1966); (ii) Schroeder and Luebke, The Peptide, Academic Press. New York (1965); (iii) Nobuo Izumiya et al., Peptide Gosei no Kiso to Jikken (Fundamentals and Experiments in Peptide Synthesis), Maruzen, Ltd. (1975); (iv) Haruaki Yajima and Shunpei Sakakibara, Seikagaku Jikken Koza (Biochemical Experiment Series) 1, Tanpakushitu no Kagaku (Protein Chemistry) IV, p. 205 (1977); (v) Hamaki Yajima (ed.), Zoku Iyakuhin no Kaihatsu (Drug Development, Continued), vol. 14, Peptide Synthesis, Hirokawa Shoten, etc.).

After completion of the reaction, the protein/peptide of the present invention can be purified and isolated by using such techniques as solvent extraction, distillation, column chromatography, liquid chromatography, recrystallization, etc. in a suitable combination. When the protein/peptide obtained by the methods described above is a free form, the free form can be converted to an appropriate salt by a known method or its modifications; conversely when the protein/peptide is obtained in the form of a salt, the salt can be converted into a free form or another salt by a known method or its modifications. The MIF and modified MIF may be further modified through glycosylation, phosphorylation, carbonylation, ubiquitinization, acetylation, methylation, lipid modification, etc. by a known method, as long as they maintain the ARE activation activity or/and cell death inhibitory activity.

2. ARE Activator Comprising the Combination of MIR or its Modified Form and the Substance Capable of Binding to MIF The present invention further includes the ARE activator comprising the combination of MIF or its modified form and the substance capable of binding to MIF (hereinafter sometimes referred to as the bindable substance).

The MIF or modified MIF described above can be used as MIF or its modified form. In the ARE activator comprising the combination of MIF or its modified form and the bindable substance, it is preferred that the first amino acid in MIF or its modified form represented by SEQ ID NO: 1 or SEQ ID NO: 7 is Pro. Furthermore, it is preferred that the N-terminal amino acid in MIF or its modified form represented by SEQ ID NO: 1 or SEQ ID NO: 7 is Pro. The phrase "comprising the combination of MIF or its modified form and the substance capable of binding to MIF" means not only a case where MIF or its modified form is covalently bound to the substance capable of binding to MIF but also a case where they are bound to each other in a mutually hydrophobic, electrical or ionic interactive state.

(Substance Capable of Binding to or Activating MIF or its Modified Form)

The substance capable of binding to MIF or its modified form may be any substance as long as the substance is capable of binding to MIF or its modified form, and may be any substance that can regulate the functions of MIF or its modified form. The substance includes, for example, a substance capable of activating MIF.

The substance capable of binding to MIF includes, for example, a 5- to 8-membered cyclic compound which may optionally be substituted and contains at least one carbon atom in the atoms constituting the ring, a 5- to 8-membered bicyclic compound, each of which ring may optionally be substituted and contains at least one carbon atom in the atoms constituting the ring, etc. Herein, the substituent includes the same substituents given for $R^1$ or $R^2$ in the formula of the 1,3-benzothiazinone derivative.

The substance capable of binding to MIF includes, for example, (a) an antibody against MIF, (b) the 1,3-benzothiazinone derivative, etc.

Preferably, the bindable substance is the 1,3-benzothiazinone derivative. As described above, where the bindable substance is the 1,3-benzothiazinone derivative, it is preferred that the first amino acid in MIF represented by SEQ ID NO: 1 or SEQ ID NO: 7 or its modified form is Pro; it is also preferred that the N-terminal amino acid in MIF or its modified form represented by SEQ ID NO: 1 or SEQ ID NO: 7 is Pro.

The substance capable of activating MIF includes, for example, (b) the 1,3-benzothiazinone derivative, etc.

The antibody against MIF may be any antibody so far as the antibody specifically reacts with MIF and includes a polyclonal antibody or a monoclonal antibody, preferably a monoclonal antibody. The antibody can be produced according to known methods of producing antibodies or antisera using MIF as an antigen.

1,3-Benzothiazinone derivative

The 1,3-benzothiazinone derivative includes the compounds represented by formula:

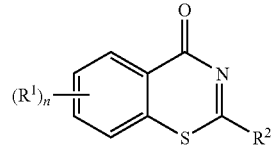

(I)

(wherein $R^1$ represents hydrogen atom, a halogen atom, hydroxy, nitro, an alkyl which may optionally be halogenated, an alkoxy which may optionally be substituted, an acyl or an amino which may optionally be substituted;

R² represents a hydrocarbon group which may optionally be substituted, an aromatic heterocyclic group which may optionally be substituted, or an amino which may optionally be substituted; and n represents 1 or 2) or salts thereof, the compounds described in WO 03/20719, WO 03/90782, WO 2006-132438, and the like.

In the formula above, R¹ represents hydrogen atom, a halogen atom, hydroxy, nitro, an alkyl which may optionally be halogenated, an alkoxy which may optionally be substituted, an acyl, or an amino which may optionally be substituted.

The "halogen atom" shown by R¹ includes, for example, fluorine, chlorine, bromine, iodine, etc.

The "alkyl which may optionally be halogenated" shown by R¹ includes, for example, an alkyl which may optionally have 1 to 5, preferably 1 to 3 halogen atoms (e.g., fluorine, chlorine, bromine, iodine, etc.) (e.g., $C_{1-6}$ alkyl such as methyl, ethyl, propyl, isopropyl, butyl, isobutyl, sec-butyl, tert-butyl, pentyl, hexyl, etc.), and the like. Specific examples are methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.

The "alkoxy" in the "alkoxy which may optionally be substituted" shown by R¹ includes, for example, $C_{1-8}$ alkoxy such as methoxy, ethoxy, propoxy, isopropoxy, butoxy, isobutoxy, sec-butoxy, pentyloxy, hexyloxy, etc.

The "substituent" in the "alkoxy which may optionally be substituted" shown by R¹ includes the "substituents" given for the "hydrocarbon group which may optionally be substituted" shown by R³ later described and 1 to 3 of the substituents are used at the substitutable positions.

The acyl shown by R¹ includes, for example, an acyl represented by formula: —(C=O)—R³, —(C=O)—OR³, —(C=O)—NR³R⁴, —(C=S)—NHR³, —SO—R⁵, —SO₂—R⁵ or —SO₂—NHR³ [wherein, R³ is hydrogen atom or a hydrocarbon group which may optionally be substituted or a heterocyclic group which may optionally be substituted, R⁴ is hydrogen atom or $C_{1-6}$ alkyl, and R⁵ is a hydrocarbon group which may optionally be substituted or a heterocyclic group which may optionally be substituted].

In the formula described above, the "hydrocarbon group" in the "hydrocarbon group which may optionally be substituted" shown by R³ includes, for example, a linear or cyclic hydrocarbon group (e.g., alkyl, alkenyl, alkynyl, cycloalkyl, aryl, aralkyl, etc.), and the like. Of these groups, a linear or cyclic hydrocarbon group having 1 to 16 carbon atoms is preferred.

Preferred examples of the "alkyl" are $C_{1-6}$ alkyl (e.g., methyl, ethyl, propyl, isopropyl, butyl, isobutyl, sec-butyl, tert-butyl, pentyl, hexyl, etc.) and the like.

Preferred examples of the "alkenyl" are $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.) and the like.

Preferred examples of the "alkynyl" are $C_{2-6}$ alkynyl (e.g., ethynyl, propargyl, 1-butynyl, 2-butynyl, 3-butynyl, 1-hexynyl, etc.) and the like.

Preferred examples of the "cycloalkyl" are $C_{3-6}$ cycloalkyl (e.g., cyclopropyl, cyclobutyl, cyclopentyl, cyclohexyl, etc.) and the like.

Preferred examples of the "aryl" are $C_{6-14}$ aryl (e.g., phenyl, 1-naphthyl, 2-naphthyl, 2-biphenylyl, 3-biphenylyl, 4-biphenylyl, 2-anthryl, etc.) and the like.

Preferred examples of the "aralkyl" are $C_{7-16}$ aralkyl (e.g., benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, etc.) and the like.

The "substituent" in the "hydrocarbon group which may optionally be substituted" shown by R³ includes, for example, a halogen atom (e.g., fluorine, chlorine, bromine, iodine, etc.), $C_{1-3}$ alkylenedioxy (e.g., methylenedioxy, ethylenedioxy, etc.), nitro, cyano, $C_{1-6}$ alkyl which may optionally be halogenated, $C_{2-6}$ alkenyl which may optionally be halogenated, carboxy $C_{2-6}$ alkenyl (e.g., 2-carboxylethenyl, 2-carboxy-2-methylethenyl, etc.), $C_{2-6}$ alkynyl which may optionally be halogenated, $C_{3-4}$ cycloalkyl which may optionally be halogenated, $C_{6-14}$ aryl (e.g., phenyl, 1-naphthyl, 2-naphthyl, 2-biphenylyl, 3-biphenylyl, 4-biphenylyl, 2-anthryl, etc.), $C_{1-8}$ alkoxy which may optionally be halogenated, $C_{1-6}$ alkoxy-carbonyl-$C_{1-6}$ alkoxy (e.g., ethoxycarbonylmethyloxy, etc.), hydroxy, $C_{6-14}$ aryloxy (e.g., phenyloxy, 1-naphthyloxy, 2-naphthyloxy, etc.), $C_{7-16}$ aralkyloxy (e.g., benzyloxy, phenethyloxy, etc.), mercapto, $C_{1-6}$ alkylthio which may optionally be halogenated, $C_{6-14}$ arylthio (e.g., phenylthio, 1-naphthylthio, 2-naphthylthio, etc.), $C_{7-16}$ aralkylthio (e.g., benzylthio, phenethylthio, etc.), amino, mono-$C_{1-6}$ alkylamino (e.g., methylamino, ethylamino, etc.), mono-$C_{6-14}$ arylamino (e.g., phenylamino, 1-naphthylamino, 2-naphthylamino, etc.), di-$C_{1-6}$ alkylamino (e.g., dimethylamino, diethylamino, ethylmethylamino, etc.), di-$C_{6-14}$ arylamino (e.g., diphenylamino, etc.), formyl, carboxy, $C_{1-6}$ alkyl-carbonyl (e.g., acetyl, propionyl, etc.), $C_{3-4}$ cycloalkyl-carbonyl (e.g., cyclopropylcarbonyl, cyclopentylcarbonyl, cyclohexylcarbonyl, etc.), $C_{1-6}$ alkoxy-carbonyl (e.g., methoxycarbonyl, ethoxycarbonyl, propoxycarbonyl, tert-butoxycarbonyl, etc.), $C_{6-14}$ aryl-carbonyl (e.g., benzoyl, 1-naphthoyl, 2-naphthoyl, etc.), $C_{7-16}$ aralkyl-carbonyl (e.g., phenylacetyl, 3-phenylpropionyl, etc.), $C_{6-14}$ aryloxy-carbonyl (e.g., phenoxycarbonyl, etc.), $C_{7-16}$ aralkyloxy-carbonyl (e.g., benzyloxycarbonyl, phenethyloxycarbonyl, etc.), a 5- or 6-membered heterocyclic carbonyl (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), carbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{1-6}$ alkyl-carbamoyl which may optionally be aminated, $C_{6-14}$ aryl-carbamoyl (e.g., phenylcarbamoyl, 1-naphthylcarbamoyl, 2-naphthylcarbamoyl, etc.), 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), $C_{1-6}$-alkylsulfonyl (e.g., methylsulfonyl, ethylsulfonyl, etc.), $C_{6-14}$ arylsulfonyl (e.g., phenylsulfonyl, 1-naphthylsulfonyl, 2-naphthylsulfonyl, etc.), formylamino, $C_{1-6}$ alkyl-carbonylamino (e.g., acetylamino, etc.), $C_{6-14}$ aryl-carbonylamino (e.g., benzoylamino, naphthylamino, etc.), $C_{1-6}$ alkoxy-carbonylamino (e.g., methoxycarbonylamino, ethoxycarbonylamino, propoxycarbonylamino, butoxycarbonylamino, etc.), $C_{1-6}$ alkylsulfonylamino (e.g., methylsulfonylamino, ethylsulfonylamino, etc.), $C_{6-14}$ arylsulfonylamino (e.g., phenylsulfonylamino, 2-naphthylsulfonylamino, 1-naphthylsulfonylamino, etc.), $C_{1-6}$ alkyl-carbonyloxy (e.g., acetoxy, propionyloxy, etc.), $C_{6-14}$ aryl-carbonyloxy (e.g., benzoyloxy, naphthylcarbonyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), $C_{6-14}$ aryl-carbamoyloxy (e.g., phenylcarbamoyloxy, naphthylcarbamoyloxy, etc.), nicotinoyloxy, 5- to 7-membered saturated cyclic amino which may optionally be substituted, 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), sulfo, and the like.

The "hydrocarbon group" may have, for example, 1 to 5, preferably 1 to 3, of the above substituents at substitutable positions. Where the number of substituents is 2 or more, the respective substituents may be the same or different.

The "$C_{1-6}$ alkyl which may optionally be halogenated" described above includes alkyl (e.g., $C_{1-6}$ alkyl such as methyl, ethyl, propyl, isopropyl, butyl, isobutyl, sec-butyl, tert-butyl, pentyl, hexyl, etc.) which may optionally have, for example, 1 to 5, preferably 1 to 3 halogen atoms (e.g., fluorine, chlorine, bromine, iodine, etc.), and the like. Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, and the like.

The "$C_{2-6}$ alkenyl which may optionally be halogenated" described above includes $C_{2-6}$ alkenyl (e.g., vinyl, propenyl, isopropenyl, 2-buten-1-yl, 4-penten-1-yl, 5-hexen-1-yl, etc.) which may optionally have, for example, 1 to 5, preferably 1 to 3 halogen atoms (e.g., fluorine, chlorine, bromine, iodine, etc.), and the like.

The "$C_{2-6}$ alkynyl which may optionally be halogenated" described above includes $C_{2-6}$ alkynyl (e.g., 2-butyn-1-yl, 4-pentyn-1-yl, 5-hexyn-1-yl, etc.), which may optionally have, for example, 1 to 5, preferably 1 to 3 halogen atoms (e.g., fluorine, chlorine, bromine, iodine, etc.), and the like.

The "$C_{3-4}$ cycloalkyl which may optionally be halogenated" described above includes $C_{3-4}$ cycloalkyl (e.g., cyclopropyl, cyclobutyl, cyclopentyl, cyclohexyl, etc.), which may optionally have, for example, 1 to 5, preferably 1 to 3 halogen atoms (e.g., fluorine, chlorine, bromine, iodine, etc.), and the like. Specific examples are cyclopropyl, cyclobutyl, cyclopentyl, cyclohexyl, 4,4-dichlorocyclohexyl, 2,2,3,3-tetrafluorocyclopentyl, 4-chlorocyclohexyl, etc.

The "$C_{1-8}$ alkoxy which may optionally be halogenated" described above includes $C_{1-8}$ alkoxy (e.g., methoxy, ethoxy, propoxy, isopropoxy, butoxy, isobutoxy, sec-butoxy, pentyloxy, hexyloxy, etc.), which may optionally have, for example, 1 to 5, preferably 1 to 3 halogen atoms (e.g., fluorine, chlorine, bromine, iodine, etc.), and the like. Specific examples are methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, and the like.

The $C_{1-6}$ alkylthio which may optionally be halogenated" described above includes $C_{1-6}$ alkylthio (e.g., methylthio, ethylthio, propylthio, isopropylthio, butylthio, sec-butylthio, tert-butylthio, etc.), which may optionally have, for example, 1 to 5, preferably 1 to 3 halogen atoms (e.g., fluorine, chlorine, bromine, iodine, etc.), and the like. Specific examples are methylthio, difluoromethylthio, trifluoromethylthio, ethylthio, propylthio, isopropylthio, butylthio, 4,4,4-trifluorobutylthio, pentylthio, hexylthio, and the like.

In the "5- to 7-membered saturated cyclic amino which may optionally be substituted" described above, the "5- to 7-membered saturated cyclic amino" includes, for example, 5- to 7-membered saturated cyclic amino optionally containing 1 to 4 hetero atoms of one or two species selected from nitrogen, sulfur and oxygen atoms, in addition to one nitrogen atom and carbon atom. Specific examples are pyrrolidin-1-yl, piperidino, piperazin-1-yl, morpholino, thiomorpholino, tetrahydroazepine-1-yl, etc.

In the "5- to 7-membered saturated cyclic amino which may optionally be substituted" described above, the "substituent" may be 1 to 3 and include, for example, $C_{1-6}$ alkyl (e.g., methyl, ethyl, propyl, isopropyl, butyl, isobutyl, sec-butyl, tert-butyl, pentyl, hexyl, etc.), $C_{1-14}$ aryl (e.g., phenyl, 1-naphthyl, 2-naphthyl, 2-biphenylyl, 3-biphenylyl, 4-biphenylyl, 2-anthryl, etc.), $C_{1-6}$ alkyl-carbonyl (e.g., acetyl, propionyl, etc.), 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), oxo, and the like.

In the "heterocyclic group which may optionally be substituted" shown by $R^3$, the "heterocyclic group" includes, for example, a monovalent group formed by removing optional one hydrogen atom from a 5- to 14-membered (mono-, bi- or tricyclic) hetero ring containing 1 to 4 hetero atoms of one or two species selected from nitrogen, sulfur and oxygen atoms, in addition to the carbon atoms, preferably (i) a 5- to 14-membered (preferably 5- to 10-membered) aromatic hetero ring, (ii) a 5- to 10-membered non-aromatic hetero ring, or (iii) a 7- to 10-membered bridged-hetero ring.

The "5- to 14-membered (preferably 5- to 10-membered) aromatic hetero ring" includes, for example, aromatic hetero rings such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthylidine, quinoxaline, quinazoline, cinnoline, carbazole, β-carboline, phenanthridine, acridine, phenazine, thiazole, isothiazole, phenothiazine, isoxazole, furazane, pbenoxazine, etc., or rings formed by condensing one or more of these rings (preferably a monocyclic ring) with one or more (preferably 1 or 2) aromatic rings (e.g., benzene ring, etc.), and the like.

The "5- to 10-membered non-aromatic hetero ring" described above includes, for example, pyrrolidine, imidazoline, pyrazolidine, pyrazoline, piperidine, piperazine, morpholine, thiomorpholine, dioxazole, oxadiazoline, thiadiazoline, triazoline, thiadiazole, dithiazole, and the like.

The "7- to 10-membered bridged-hetero ring" includes, for example, quinuclidine, 7-azabicyclo[2.2.1]heptane, and the like.

The "heterocyclic group" is preferably a 5- to 14-membered (preferably 5- to 10-membered) (monocyclic or bicyclic) heterocyclic group containing preferably 1 to 4 hetero atoms of one or two species selected from nitrogen, sulfur and oxygen atoms, in addition to the carbon atoms. Specific examples are an aromatic heterocyclic group such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.; a non-aromatic heterocyclic group such as 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino, etc.

Among them, more preferred are, for example, 5- or 6-membered heterocyclic groups containing 1 to 3 hetero atoms selected from nitrogen, sulfur and oxygen atom in addition to the carbon atoms, and the like. Specific examples include 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino, etc.

The "substituent" in the "optionally substituted heterocyclic group" includes the same substituents exemplified as the "substituents" in the "hydrocarbon group which may optionally be substituted" shown by $R^3$ described above.

The "heterocyclic group" may have, for example, 1 to 5, preferably 1 to 3, of the above substituents at substitutable positions. Where the number of substituents is 2 or more, the respective substituents may be the same or different.

The "$C_{1-6}$ alkyl" shown by $R^4$ includes, for example, methyl, ethyl, propyl, isopropyl, butyl, isobutyl, sec-butyl, tert-butyl, pentyl, hexyl, and the like.

The "hydrocarbon group which may optionally be substituted" and "heterocyclic group which may optionally be substituted" represented by $R^5$ include, for example, the "hydrocarbon group which may optionally be substituted" and "heterocyclic group which may optionally be substituted" represented by $R^3$ described above, respectively.

The "substituent" in the "amino group which may optionally be substituted" represented by $R^1$ may be 1 or 2 and includes the "substituents" given for the "hydrocarbon group which may optionally be substituted" represented by $R^3$ described above.

Specific examples of $R^1$ are (1) hydrogen atom, (2) a halogen atom, (3) hydroxy, (4) $C_{1-6}$ alkyl which may optionally be halogenated, (5) $C_{1-6}$ alkoxy which may have a substituent(s) selected from carboxy, hydroxy, $C_{1-6}$ alkoxy-carbonyl and $C_{6-10}$ aryl, (6) $C_{1-6}$ alkyl-carbamoyl, (7) $C_{3-4}$ cycloalkyl-carbamoyl, (8) 5- or 6-membered saturated cyclic amino-carbonyl, and the like.

Preferred examples of $R^1$ are hydrogen atom, a halogen atom, an alkyl (preferably $C_{1-6}$ alkyl) which may optionally be halogenated, or an alkoxy (preferably $C_{1-6}$ alkoxy) which may optionally be halogenated, and the like. Particularly preferred is hydrogen atom.

The "hydrocarbon group which may optionally be substituted" and "heterocyclic group which may optionally be substituted" represented by $R^2$ include, for example, the "hydrocarbon group which may optionally be substituted" and "heterocyclic group which may optionally be substituted" represented by $R^3$ described above, respectively.

The "amino group which may optionally be substituted" represented by $R^2$ includes the "amino which may optionally be substituted" represented by $R^1$ described above.

Preferred examples of $R^2$ include aromatic heterocyclic rings [e.g., pyridyl, furyl, thienyl, pyrrolyl, quinolyl, pyrazinyl, pyrimidinyl, pyridazinyl, indolyl, tetrahydroquinolyl or thiazolyl (preferably pyridyl and more preferably 2- or 4-pyridyl)], etc., each ring having 1 to 3 substituents selected from:

(1) a halogen atom;
(2) $C_{1-6}$ alkyl which may optionally have 1 to 5 substituents selected from (i) a halogen atom, (ii) hydroxy, (iii) carboxy, (iv) cyano, (v) carboxy-$C_{1-6}$ alkoxy, (vi) $C_{1-6}$ alkoxy-$C_{1-6}$ alkoxy, (vii) $C_{1-6}$ alkoxy-carbonyl-$C_{1-6}$ alkoxy, (viii) $C_{1-6}$ alkyl-carbonyloxy, (ix) $C_{1-6}$ alkoxy-carbonyl, (x) a carbamoyl which may optionally have 1 or 2 substituents selected from (a) mono- or di-$C_{1-6}$ alkyl which may optionally have carboxy, (b) $C_{1-6}$ alkylsulfonyl and (c) $C_{6-10}$ arylsulfonyl, (xi) 5- or 6-membered saturated cyclic amino-carbonyl which may optionally have carboxy, (xii) $C_{1-6}$ alkylthio which may optionally have $C_{1-6}$ alkoxy-carbonyl, (xiii) $C_{1-6}$ alkylsulfinyl which may optionally have $C_{1-6}$ alkoxy-carbonyl, (xiv) $C_{1-6}$ alkylsulfonyl which may optionally have $C_{1-6}$ alkoxy-carbonyl, (xv) $C_{7-12}$ aralkylthio, (xvi) $C_{7-12}$ aralkylsulfinyl, (xvii) $C_{7-12}$ aralkylsulfonyl, (xviii) 5- or 6-membered aromatic heterocyclic thio, (xix) amino which may optionally have 1 or 2 substituents selected from (a) $C_{1-6}$ alkyl, (b) $C_{1-6}$ alkoxy-carbonyl, (c) $C_{1-6}$ alkyl-carbonyl which may optionally be halogenated, (d) $C_{6-10}$ aryl-carbonyl, (e) thienylcarbonyl, (f) $C_{1-6}$ alkylthio-$C_{1-6}$ alkyl-carbonyl, (g) mono- or di-$C_{1-6}$ alkyl-carbamoyl, (h) $C_{1-6}$ alkylsulfonyl, (i) $C_{6-10}$ arylsulfonyl, (j) di-$C_{1-6}$ alkylphosphono, (k) di-$C_{1-6}$ alkylthiophosphono and (l) $C_{6-10}$ aryl-carbamoyl, (xx) phthalimide, (xxi) $C_{1-6}$ alkylsulfonyloxy, (xxii) 5- or 6-membered aromatic heterocyclic group, (xxiii) phosphono which may optionally have $C_{1-6}$ alkyl, (xxiv) 5- to 7-membered saturated cyclic amino which may optionally have 1 or 2 substituents selected from (a) $C_{7-12}$ aralkyl, (b) $C_{6-10}$ aryl which may optionally be halogenated and (c) hydroxy, and (xxv) 5- to 7-membered cyclic amino-carbonyl;
(3) $C_{1-6}$ alkenyl which may optionally have carboxy or $C_{1-6}$ alkoxy-carbonyl;
(4) $C_{6-10}$ aryl which may optionally have $C_{1-6}$ alkoxy;
(5) $C_{1-6}$ alkoxy which may optionally have a substituent selected from $C_{1-6}$ alkoxy, $C_{1-6}$ alkoxy-carbonyl, phthalimide, di-$CO_{1-6}$ alkylsulfonamide and di-$C_{1-6}$ alkylaminomethylenesulfonamide;
(6) $C_{6-10}$ aryloxy which may optionally have $C_{1-6}$ alkylthio;
(7) $C_{7-12}$ aralkyloxy;
(8) $C_{1-6}$ alkylthio which may optionally have a substituent selected from mono- or di-$C_{1-6}$ alkylamino, carboxy, carbamoyl and $C_{1-6}$ alkoxy-carbonyl;
(9) $C_{1-6}$ alkylsulfinyl which may optionally have mono- or di-$C_{1-6}$ alkylamino, carboxy, carbamoyl and $C_{1-6}$ alkoxy-carbonyl;
(10) $C_{1-6}$ alkylsulfonyl which may optionally have a substituent selected from mono- or di-$C_{1-6}$ alkylamino, carboxy and $C_{1-6}$ alkoxy-carbonyl;
(11) $C_{6-10}$ arylthio which may optionally have a substituent selected from a halogen atom, $C_{1-6}$ alkyl and $C_{1-6}$ alkoxy-carbonyl;
(12) $C_{6-10}$ arylsulfinyl which may optionally have $C_{1-6}$ alkyl;
(13) $C_{6-10}$ arylsulfonyl which may optionally have $C_{1-6}$ alkyl;
(14) carboxy;
(15) $C_{1-6}$ alkoxy-carbonyl;
(16) $C_{7-12}$ aralkylthio;
(17) $C_{7-12}$ aralkylsulfinyl;
(18) $C_{7-12}$ aralkylsulfonyl;
(19) amino which may optionally have 1 or 2 substituents selected from $C_{1-6}$ alkyl, $C_{7-12}$ aralkyl, $C_{1-6}$ alkoxy-$C_{1-6}$ alkyl, $C_{1-6}$ alkoxycarbonyl, $C_{1-6}$ alkoxycarbonyl-$C_{1-6}$ alkyl, carboxy-$C_{1-6}$ alkyl, $C_{1-6}$ alkylcarbonyl, $C_{6-10}$ aryl-carbonyl, $C_{3-6}$ cycloalkylcarbonyl, thienylcarbonyl, furylcarbonyl and mono- or di-$C_{1-6}$ alkylaminocarbonyl;
(20) 5- to 7-membered saturated cyclic amino which may optionally have a substituent selected from (i) $C_{6-10}$ aryl which may optionally be halogenated, (ii) $C_{7-12}$ aralkyl, (iii) hydroxy, (iv) $C_{1-6}$ alkyl which may optionally have $C_{1-6}$ alkoxycarbonyl or carboxy, (v) oxo, (vi) $C_{1-6}$ alkyl-carbonyl, (vii) $C_{6-10}$ aryl-carbonyl and (viii) $C_{1-6}$ alkoxycarbonyl;

(21) carbamoyl which may optionally have a substituent selected from (i) $C_{1-6}$ alkyl which may optionally have a substituent selected from a halogen atom, $C_{1-6}$ alkoxy, amino, $C_{1-6}$ alkoxy-carboxamido and hydroxy, (ii) $C_{7-12}$ aralkyl and (iii) mono- or di-$C_{1-6}$ alkylamino-carbonyl;

(22) 5- to 7-membered cyclic amino-carbonyl;

(23) 5- or 6-membered aromatic heterocyclic group which may optionally have $C_{1-6}$ alkyl;

(24) cyano;

(25) 5- to 10-membered aromatic heterocyclic group-thio which may optionally have $C_{1-6}$ alkyl;

(26) $C_{1-6}$ alkylcarbonyl; and,

(27) oxo.

The pyridyl may also be N-oxidized. A preferred substituent of the pyridyl is $C_{1-6}$ alkyl-carbonyl which may optionally be aminated.

More preferably, $R^2$ includes pyridyl, furyl, thienyl, pyrrolyl, quinolyl, pyrazinyl, pyrimidinyl, pyridazinyl, indolyl, tetrahydroquinolyl or thiazolyl (preferably pyridyl, more preferably 2- or 4-pyridyl), etc., which may optionally have 1 to 3 substituents selected from (1) $C_{1-6}$ alkyl which may optionally have a substituent selected from $C_{1-6}$ alkoxycarbonyl-$C_{1-6}$ alkoxy, carboxy-$C_{1-6}$ alkoxy, carboxy, $C_{1-6}$ alkoxycarbonyl and $C_{1-6}$ alkylsulfonyloxy, (2) $C_{1-6}$ alkenyl which may optionally have carboxy or $C_{1-6}$ alkoxy-carbonyl, (3) $C_{1-6}$ alkylthio which may optionally have mono- or di-$C_{1-6}$ alkylamino or $C_{1-6}$ alkoxycarbonyl, (4) $C_{1-6}$ alkylsulfinyl which may optionally have mono- or di-$C_{1-6}$ alkylamino, (5) $C_{1-6}$ alkylsulfonyl which may optionally have mono- or di-$C_{1-6}$ alkylamino, (6) $C_{7-12}$ aralkylthio, (7) $C_{7-12}$ aralkylsulfinyl, (8) $C_{7-12}$ aralkylsulfonyl, (9) carbamoyl which may optionally have a substituent selected from (i) $C_{1-6}$ alkyl which may optionally have a substituent selected from a halogen atom, $C_{1-6}$ alkoxy and amino, (ii) $C_{7-12}$ aralkyl and (iii) mono- or di-$C_{1-6}$ alkylamino-carbonyl, and (10) 5- to 7-membered cyclic amino-carbonyl. The pyridyl may also be N-oxidized. A preferred substituent of the pyridyl is $C_{1-6}$ alkyl-carbonyl which may optionally be aminated.

Preferred "salts" of the compound represented by formula (I) are pharmaceutically acceptable salts and include, for example, salts with inorganic bases, salts with organic bases, salts with inorganic acids, salts with organic acids, salts with basic or acidic amino acids, etc. Preferred examples of the salts with inorganic bases are alkali metal salts such as sodium salts, potassium salts; alkaline earth metal salts such as calcium salts, magnesium salts, etc.; aluminum salts, ammonium salts, and the like. Preferred examples of the salts with organic bases are salts with trimethylamine, triethylamine, pyridine, picoline, ethanolamine, diethanolamine, triethanolamine, dicyclohexylamine, N,N'-dibenzylethylenediamine, etc. Preferred examples of the salts with inorganic acids are salts with hydrochloric acid, hydrobromic acid, nitric acid, sulfuric acid, phosphoric acid, etc. Preferred examples of the salts with organic acids are salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids are salts with arginine, lysine, ornithine, etc. and preferred examples of the salts with acidic amino acids are salts with aspartic acid, glutamic acid, etc.

When the compound represented by formula (I) exists as configurational isomers (positional isomers), diastereomers, conformers, etc., each can be isolated, if necessary, by any of the techniques for isolation or purification described above.

Further when the compound represented by formula (I) is a racemate, it can be separated into (S) and (R) forms by a conventional means of optical resolution.

Where stereoisomers exist in the compound represented by formula (I), these isomers, either alone or as an admixture thereof, are also within the scope of the present invention.

The compound represented by formula (I) may be purchased when it is commercially available, or can be produced by per se known methods or modifications thereof. Reference can be made to, for example, WO 03/20719, WO 03/90782, WO 2006-132438, etc., for details of the 1,3-benzothiazinone derivative and its production methods.

(Pharmacological Activities, Therapeutic Use, Etc., of MIF or its Modified Form)

MIF or its modified form can suppress cell death since it has the activities of inducing the expression of cell protective factors (e.g., heme oxygenase-1, etc.) and activating ARE. In addition, MIF or its modified form can attenuate adverse effects caused by drugs (e.g., anticancer agents, HMG-CoA reductase inhibitors, etc.). The ARE activator comprising the combination of MIF or its modified form and the bindable substance can suppress cell death because it induces the expression of cell protective factors (e.g., heme oxygenase-1, etc.) and has the ARE activation activity. Furthermore, the ARE activator can also attenuate adverse effects caused by drugs (e.g., anticancer agents, HMG-CoA reductase inhibitors, etc.).

Also MIF or its modified form has the ARE activation activity so that it can induce the expression of cell protective factors (e.g., heme oxygenase-1, etc.) and suppress cell death. Moreover, MIF or its modified form can also attenuate adverse effects caused by drugs (e.g., anticancer agents, HMG-CoA reductase inhibitors, etc.). The ARE activator comprising the combination of MIF or its modified form and the bindable substance has the ARE activation activity thereby to induce the expression of cell protective factors (e.g., heme oxygenase-1, etc.) and hence can suppress cell death. Furthermore, the ARE activator can also attenuate adverse effects caused by drugs (e.g., anticancer agents, HMG-CoA reductase inhibitors, etc.). By these activities, (a) MIF or its modified form or (b) the combination of MIF or its modified form and the substance capable of binding to MIF is useful as a safe and low-toxic ARE activator (e.g., an ARE gene expression promoting agent, a promoting agent for the expression of ARE protein, a promoting agent for the activity of ARE protein, a promoting agent for the gene (e.g., heme oxygenase-1, liver glutathione S-transferase Ya subunit, liver glutathione S-transferase Yc subunit, glutathione S-transferase Yb subunit, glutathione S-transferase Yc1 subunit, gamma-glutamylcysteine synthetase, NAD(P)H:quinone reductase, UDP-glucuronosyltransferase, exon 1, bilirubin-specific UDP-glucuronosyltransferase, NAD(P)H-menadione oxidoreductase, etc.) under control of ARE, an agent for upregulating (promoting) the production or for promoting the activity of gene protein (gene product) under control of ARE, etc., a cell death inhibitor (e.g., inhibitors of cell death induced by oxidative stress, cell death induced by serum deprivation, cell death induced by growth factor depletion, cell death induced by HMG-CoA reductase inhibitors, cell death induced by anticancer drugs, cell death induced by NO, cell death induced by amyloid β protein, etc.), cytoprotective agent, etc., for example, as an agent for the prevention/treatment of cardiovascular diseases [e.g., myocardiopathy (e.g., dilated cardiomyopathy, hypertrophic obstructive cardiomyopathy, hypertrophic nonobstructive cardiomyopathy, idiopathic cardiomyopathy, constrictive cardiomyopathy, diabetic cardiomyopathy, etc.), heart failure (e.g., chronic heart failure, chronic congestive heart failure, acute heart failure, compensated heart failure, left heart failure, right heart failure, congestive heart failure, acute congestive heart failure, metabolic heart failure, dilated heart failure, high-output heart failure, low-output heart failure, intractable heart failure, poor prognosis of myocardial infarction, etc.), angina pectoris, myocardial infarction, arteriosclerosis (aneurysm, coronary atherosclerosis, cerebral atherosclerosis, peripheral arteriosclerosis, etc.), post-ischemia-reperfusion injury, etc.], bone/joint diseases [e.g., chronic articular rheumatism, degenerative arthritis, knee osteoarthritis, etc.], infectious diseases [e.g., viral infections with cytomegalovirus, influenza virus, herpes virus, etc., rickettsial infection, bacterial infection, etc.], inflammatory diseases [e.g., diabetic complications including retinopathy, nephropathy, neuropathy, macroangiopathy, etc.; arthritis including rheumatoid myelitis, periostitis, etc.; post-operative/post-traumatic inflammation; remission of swelling; pharyngitis; cystitis; pneumonia; atopic dermatitis; Crohn's disease, inflammatory bowel diseases such as ulcerative colitis, etc.; meningitis; inflammatory ophthalmopathy; inflammatory pulmonary diseases including pneumonia, silicosis, pulmonary sarcoidosis, pulmonary tuberculosis, etc.], renal diseases [e.g., organ dysfunctions including ischemic acute renal failure, hemolytic-uremic syndrome, acute tubular necrosis, hydronephrosis, nephritis, glomerulonephritis, glomerulosclerosis, renal failure, thrombotic microangiopathy, renal transplant rejection, dialysis complications, nephropathy induced by radiation, etc.], central nervous diseases [e.g., neurodegenerative disorders (e.g., Alzheimer's disease, Parkinson's disease, Huntington's chorea, polyglutamine disease, amyotrophic lateral sclerosis, AIDS encephalopathy, etc.), central nervous system disorders (sequelae/complications including cerebral hemorrhage, cerebral infarction, etc., head injury, spinal cord injury, cerebral edema, impaired sensory function, sensory dysfunction, impaired autonomic function, autonomic dysfunction, multiple sclerosis, etc.), dementia, memory impairment, impairment of consciousness, amnesia, anxiety symptom, catatonic syndrome, unpleasant mental status, peripheral neuropathy, etc.], cancer [e.g., colorectal cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc.], diabetes mellitus [e.g., type 1 diabetes, type 2 diabetes, complications (diabetic retinopathy, diabetic cataract, diabetic nephropathy, diabetic neuropathy, etc.), etc.] and the like.

3. Medicament Comprising MIF or its Modified Form (Single Drug) or Medicament Using MIF or its Modified Form in Combination with the Substance Capable of Binding to MIF (Concomitant Drug)

According to the present invention, MIF or its modified form can be used as a single drug comprising the same. Alternatively, MIF or its modified form can also be used in combination with the substance capable of binding to MIF.

Hereinafter, the usage form of MIF or its modified form in combination with the substance capable of binding to MIF is referred to as the "concomitant drug of the present invention."

MIF or its modified form and the substance capable of binding to MIF can be safely administered orally or parenterally (e.g., topically, rectally, intravenously, etc.) to a mammal (e.g., human, monkey, etc.), each alone or as a mixture of both, in the form of a pharmaceutical composition with a pharmacologically acceptable carrier according to known methods, such as tablets (including dragees and film-coated tablets), powdery preparations, granules, capsules (including soft capsules), liquid preparations, injectable preparations, suppositories, sustained release agents, etc. The injectable preparation can be administered intravenously, intramuscularly, subcutaneously or into the organ, or directly administrated to the lesion.

The pharmaceutically acceptable carriers described above include a variety of organic or inorganic carrier materials conventionally used as materials for pharmaceutical preparations, and are mixed as excipients, lubricants, binders, disintegrators, solvents, solubilizers, suspending agents, isotonizing agents, buffers, soothing agents, etc. If necessary, additives such as conventional preservatives, antioxidants, coloring agents, sweeteners, adsorbents, wetting agents, etc. can also be used suitably.

The content of MIF or its modified form and the substance capable of binding to MIF in the preparation described above is about 0.01 to 100% by weight, based on the whole preparation.

For the use of the concomitant drug of the present invention, the timing of the administration of MIF or its modified form and the substance capable of binding to MIF is not limited. MIF or modified MIF or its pharmaceutical composition and the substance capable of binding to MIF or its pharmaceutical composition can be administered to the subject simultaneously, or may be administered at different times. The dose of the concomitant drug of the present invention may be determined according to the dose clinically used, and can be appropriately chosen depending on the subject to be administered, administration route, disease, combination, and the like.

The administration mode of the concomitant drug of the present invention is not particularly limited, and it is sufficient if MIF or its modified form and the substance capable of binding to MIF are used in combination upon administration. Examples of such administration mode include, for example, (1) administration of a single preparation obtained by simultaneous pharmaceutical manufacturing of MIF or its modified form and the substance capable of binding to MIF, (2) simultaneous administration of two kinds of preparations obtained by separate pharmaceutical manufacturing of MIF or its modified form and the substance capable of binding to MIF, through the same administration route, (3) administration of two kinds of preparations obtained by separate pharmaceutical manufacturing of MIF or its modified form and the substance capable of binding to MIF, at different time intervals, (4) simultaneous administration of two kinds of preparations obtained by separate pharmaceutical manufacturing of MIF or its modified form and the substance capable of binding to MIF, through different administration routes, (5) administration at different time intervals of two kinds of preparations obtained by separate pharmaceutical manufacturing of MIF or its modified form and the substance capable of binding to MIF, through different administration routes, etc.

The formulation ratio or use ratio of MIF or its modified form and the substance capable of binding to MIF in the concomitant drug of the present invention can be suitably chosen depending on target subject, administration route, symptoms, etc.

For example, the content of MIF or its modified form in the concomitant drug of the present invention varies depending on type of preparation and is generally about 0.01 to 100% by weight, preferably about 0.1 to 50% by weight and more preferably about 0.5 to 20% by weight based on the whole preparation.

The content of the substance capable of binding to MIF in the concomitant drug of the present invention varies depending on type of preparation and is generally about 0.01 to 100% by weight, preferably about 0.1 to 50% by weight and more preferably about 0.5 to 20% by weight, based on the whole preparation.

The content of additives such as carriers, etc. in the concomitant drug of the present invention varies depending on type of preparation and is generally about 1 to 99.99% by weight and preferably about 10 to 90% by weight, based on the whole preparation.

Also in a case where MIF or its modified form and the substance capable of binding to MIF are subjected to separate pharmaceutical manufacturing, the contents may be the same.

The dose of MIF or its modified form and the concomitant drug of the present invention vary depending upon degree of symptom; age, sex and body weight of target subject; time and interval of administration; property, dispensing and kind of pharmaceutical preparation; kind of active ingredient, etc. and is not particularly limited. When MIF or its modified form and the concomitant drug is used for the treatment of inflammatory bowel disorder, it is administered to adult at a daily dose of generally about 10 µg to about 100 mg/kg weight, preferably 100 µg to about 50 mg/kg weight as the active ingredient. The dose is usually divided and administered 1 to 4 times per day.

Herein, pharmaceutical manufacturing of the active ingredient, method of administration, etc. are described for the concomitant drug. These descriptions are also applicable to the case where the ARE activator comprising MIF or its modified form is used as a single drug.

Furthermore, the ARE activator and cell death inhibitor of the present invention can also be used in combination with HMG-CoA reductase inhibitors (e.g., Simvastatin, Atorvastatin, etc.), fibrate-type antihyperlipidemic drugs (e.g., Gemfibrozil, etc.), anticancer agents (e.g., Ifosfamide, UFT, Adriamycin, Doxorubicin, Peplomycin, Cisplatin, Cyclophosphamide, 5-FU, Methotrexate, Mitomycin C, Mitoxantrone, etc.), or the like. By the combination use, adverse effects of HMG-CoA reductase inhibitors, fibrate-type antihyperlipidemic drugs, anticancer agents, etc., which harm normal cells, are diminished.

In the specification and drawings, abbreviations for nucleotides, amino acids, etc. are based on abbreviations specified by the IUPAC-IUB Commission on Biochemical Nomenclature or abbreviations in common use in the art. Some examples are given below. When an optical isomer may be present in an amino acid, it is of the L-configuration, unless otherwise indicated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
NO: nitrogen monoxide Substituents, protecting groups and reagents frequently used in this specification are presented as the codes below.

Me: methyl
Et: ethyl
Bu: butyl
Ph: phenyl
TC: thiazolidine-4(R)-carboxamido
Tos: p-toluenesulfonyl
CHO: formyl
Bzl: benzyl
$C_2$-Bzl: 2,6-dichlorobenzyl
Bom: benzyloxymethyl
Z: benzyloxycarbonyl
Cl—Z: 2-chlorobenzyloxycarbonyl
Br—Z: 2-bromobenzyloxycarbonyl
Boc: t-butoxycarbonyl
DNP: dinitrophenyl
Trt: trityl
Bum: t-butoxymethyl
Fmoc: N-9-fluorenylmethoxycarbonyl
HOBt: 1-hydroxybenzotriazole
HOOBt: 3,4-dihydro-3-hydroxy-4-oxo-1,2,3-benzotriazine
HONB: 1-hydroxy-5-norbornene-2,3-dicarboxyimido
DCC: N,N'-dicyclohexylcarbodiimido The sequence identification numbers in the sequence listing of the specification indicate the following sequences, respectively

[SEQ ID NO: 1]
This shows the amino acid sequence of human MIF.
[SEQ ID NO: 2]
This shows the nucleotide sequence of the anti-sense strand used in REFERENCE EXAMPLE 1.
[SEQ ID NO: 3]
This shows the nucleotide sequence of the sense strand used in REFERENCE EXAMPLE 1.
[SEQ ID NO: 4]
This shows the nucleotide sequence of the anti-sense strand used in REFERENCE EXAMPLE 1.
[SEQ ID NO: 5]
This shows the nucleotide sequence of the sense strand used in REFERENCE EXAMPLE 1.
[SEQ ID NO: 6]
This shows the nucleotide sequence of ARE of rat glutathione S-transferase Ya subunit gene.
[SEQ ID NO: 7]
This shows the amino acid sequence of rat MIF.
[SEQ ID NO: 8]
This shows the nucleotide sequence of the sense strand coincident with the N terminus of rat MIF containing the NdeI cleavage site at the 5' end side, used in REFERENCE EXAMPLE 2.
[SEQ ID NO: 9]
This shows the nucleotide sequence of the anti-sense strand coincident with the C terminus of rat MIF containing the SapI cleavage site at the 5' end side, used in REFERENCE EXAMPLE 2.
[SEQ ID NO: 10]
This shows the nucleotide sequence of hMIF-5'-primer used in REFERENCE EXAMPLE 3.
[SEQ ID NO: 11]
This shows the nucleotide sequence of the hMIF-3"-primer used in REFERENCE EXAMPLE 3.
[SEQ ID NO: 12]
This shows the amino acid sequence of 30 amino acid-peptide containing histidine tag added at the N terminus, used in REFERENCE EXAMPLE 3.

[SEQ ID NO: 13]
Met His His His His His His Ser Ser Gly Leu Val
Pro Arg Gly Ser Gly Met Lys Glu Thr Ala Ala Ala
Lys Phe Glu Phe Ile Met

This shows the nucleotide sequence of the primer (TaqMan primer forward) used for quantification of rGST Ya in EXPERIMENT 4.
[SEQ ID NO: 14]
This shows the nucleotide sequence of the primer (TaqMan primer reverse) used for quantification of rGST Ya in EXPERIMENT 4.
[SEQ ID NO: 15]
This shows the nucleotide sequence of the probe (TaqMan probe) used for quantification of rGST Ya in EXPERIMENT 4.
[SEQ ID NO: 16]
This shows the nucleotide sequence of the primer (TaqMan primer forward) used for quantification of rGAPD in EXPERIMENT 4.
[SEQ ID NO: 17]
This shows the nucleotide sequence of the primer (TaqMan primer reverse) used for quantification of rGAPD in EXPERIMENT 4.
[SEQ ID NO: 18]
This shows the nucleotide sequence of the probe (TaqMan probe) used for quantification of rGAPD in EXPERIMENT 4.
[SEQ ID NO: 19]
This shows the nucleotide sequence of the primer (TaqMan primer forward) used for quantification of rHO-1 in EXPERIMENT 4.
[SEQ ID NO: 20]
This shows the nucleotide sequence of the primer (TaqMan primer reverse) used for quantification of rHO-1 in EXPERIMENT 4.
[SEQ ID NO: 21]
This shows the nucleotide sequence of the probe (TaqMan probe) used for quantification of rHO-1 in EXPERIMENT 4.

EXAMPLES

Hereinafter, the present invention will be described in detail by referring to REFERENCE EXAMPLES and EXPERIMENTS but the scope of the present invention is not deemed to be limited thereto.

Reference Example 1

Production of Human MIF Protein and its N-Terminal Modified Protein (1) Construction of Human MIF Protein and its N-Terminal Modified Protein Expression Vectors
Using a sense strand (SEQ ID NO: 5) coincident with the N terminus of human MIF containing the NdeI cleavage site at the 5' end and an antisense strand (SEQ ID NO: 2) coincident with the C terminus of human MIF containing the SapI cleavage site at the 5' end, the region encoding MIF was amplified from human complementary DNA (cDNA) library (GIBCO BRL, Inc.) by polymerase chain reaction (PCR). After the amplified MIFcDNA was cleaved with NdeI and SapI, the cleavage products were inserted between the NdeI and SapI sites of pCYB1 (IMPACT I: One-Step Protein Purification System, New England BioLabs, Inc.) to give pCYBI-hMIE.

Next, after pCYB1-hMIF was cleaved with BglI, the cleaved site was blunt ended and then further cleaved with NdeI to recover the DNA fragment encoding the fusion protein of human MIF and a intein-chitin binding domain. Next, the recovered DNA fragment was inserted between the NdeI and EcoRV sites of T7 promoter expression plasmid pET32b(+) (Novagen) to give human MIF-intein-chitin binding domain fusion protein expression plasmid pET32b-hMIF-Int-CBD. The MIFcDNA sequence in the resulting expression plasmid was confirmed using a DNA Sequence System (Applied Biosystems, Inc.).

Using a sense strand (SEQ ID NO: 3) and an anti-sense strand (SEQ ID NO: 4), an expression plasmid of the modified MIF protein (hMIF-P1S) in which the N-terminal proline (Pro1) in human MIF was replaced by serine was prepared by replacing the DNA sequence (CCG) encoding Pro1 of pET32b-hMIF-Int-CBD by the sequence (TCG) encoding serine using QuickChange Site-Directed Mutagenesis Kit (Stratagene, Inc.). The MIFcDNA sequence in the expression plasmid obtained was confirmed using a DNA Sequence System (Applied Biosystems, Inc.).
(2) Preparation of Human MIF Protein
After pET32b-hMIF-Int-CBD was transfected to Escherichia coli BL21 (DE3) (Novagen), the cells were inoculated on ampicillin-supplemented LB medium (1% tryptone, 0.5% yeast extract, 0.5% NaCl) (LBamp medium), followed by shake culture at 37° C. overnight. The cells were transferred to LBamp medium at a density of 1% and shake-cultured at 37° C. for about 2.5 hours. Then 0.4 mM isopropyl-1-thio-β-D-galactopyranoside (IPTG) was added thereto and further cultured at 15° C. for about 24 hours to induce the expression of human MIF-intein-chitin binding domain fusion protein. After completion of the incubation, Escherichia coli was recovered and suspended in a column buffer (20 mM Tris-HCl; pH 8.0, 500 mM NaCl, 0.1 mM EDTA) containing 1/10 volume of 0.1% Triton X-100, followed by ultrasonication. The cell lysate was centrifuged at 4° C. and 12000 rpm for 30 minutes to recover the supernatant. The recovered supernatant was passed through a chitin bead column (New England BioLabs, Inc.), which had been equilibrated with the column buffer containing 0.1% Triton X-100, to bind the human MIF-intein-chitin binding domain fusion protein to the column. Thereafter, the column was washed with 0.1% Triton X-100-containing column buffer in a 10-fold volume of the column size and the column buffer in a 10-fold volume of the column size to remove non-specifically bound proteins and accompanied substances. Next, the buffer within the column was replaced by a column buffer containing 50 mM dithiothreitol. The column was allowed to stand at 4° C. overnight, thereby to excise the MIF protein from the fusion protein, utilizing the protein splicing activity of intein. The excised MIF protein was eluted with the column buffer, followed by dialysis to 20 mM sodium phosphate buffer. The modified protein (hMIF-P1S) was prepared in a similar manner.

Reference Example 2

Preparation of Rat MIF Protein (1) Construction of Rat MIF Protein Expression Vector
After T7 promoter expression plasmid pET32b(+) (Novagen) was cleaved with SapI and TthIII, the cleaved site was blunt ended and then religated, whereby pET32b-1 in which the SapI cleavage site was removed from pET32b(+) was obtained. Next, pCYB1 (IMPACT I: One-Step Protein Purification System, New England BioLabs, Inc.) was cleaved with NdeI and BglI to recover the DNA fragment in the region encoding the fusion protein of multicloning site and a intein-chitin binding domain. The BglI cleavage site was blunt ended and then inserted between the NdeI and EcoRV sites of pET32b-1 to give pET32b-Int-CBD.

Next, the region encoding MIF was amplified from rat complementary DNA (cDNA) library (GIBCO BRL, Inc.) by polymerase chain reaction (PCR). For the amplification of rat MIF cDNA, a sense strand (SEQ ID NO: 8) coincident with the N terminus of rat MIF containing the NdeI cleavage site at the 5' end and an antisense strand (SEQ ID NO: 9) coincident with the C terminus of rat MIF containing the SapI cleavage site at the 5' end were used. After the amplified MIFcDNA was cleaved with NdeI and SapI, the cleavage product was inserted between the NdeI and SapI sites of pET32b-Int-CBD to give rat MIF-intein-chitin binding domain fusion protein expression plasmid pET32b-rMIF-Int-CBD. The MIFcDNA sequence in the resulting expression plasmid was confirmed using a DNA Sequence System (Applied Biosystems, Inc.).

(2) Preparation of Rat MIF Protein

After pET32b-rMIF-Int-CBD was transfected to *Escherichia coli* BL21 (DE3) (Novagen), the cells were inoculated on ampicillin-supplemented LB medium (1% tryptone, 0.5% yeast extract, 0.5% NaCl) (LBamp medium), followed by shake culture at 37° C. overnight. The cells were transferred to LBamp medium at a density of 1% and shake-cultured at 37° C. for about 2.5 hours. Then 0.4 mM isopropyl-1-thio-β-D-galactopyranoside (IPTG) was added thereto and cultured at 15° C. for further 24 hours to induce the expression of rat MIF-intein-chitin binding domain fusion protein. After completion of the incubation, *Escherichia coli* was recovered and suspended in a column buffer (20 mM Tris-HCl; pH 8.0, 500 mM NaCl, 0.1 mM EDTA) containing 1/10 volume of 0.1% Triton X-100, followed by ultrasonication. The cell lysate was centrifuged at 4° C. and 12000 rpm for 30 minutes to recover the supernatant. The recovered supernatant was passed through a chitin bead column (New England BioLabs, Inc.), which had been equilibrated with the column buffer containing 0.1% Triton X-100, to bind the rat MIF-intein-chitin binding domain fusion protein to the column. Thereafter, the column was washed with 0.1% Triton X-100-containing column buffer in a 10-fold volume of the column size and the column buffer in a 10-fold volume of the column size to remove non-specifically bound proteins and accompanied substances. Next, the buffer within the column was replaced by a column buffer containing 50 mM dithiothreitol. The column was allowed to stand at 4° C. for at least 16 hours, thereby to excise the MIF protein from the fusion protein, utilizing the protein splicing activity of intein. The excised MIF protein was eluted with the column buffer, followed by dialysis to 20 mM sodium phosphate buffer. The amino acid sequence of rat MIF protein is shown by SEQ ID NO: 7.

Reference Example 3

Preparation of N-Terminal Modified Human MIF Protein (his-hMIF) in which a Peptide Containing Histidine Tag at the N Terminus (1) Preparation of his-hMIF Expression Plasmid In a manner similar to REFERENCE EXAMPLE 1, the region encoding MIF was amplified from human complementary DNA (cDNA) library using hMIF-5' primer (5'-CG-GAATTCATCATGCCGATGTTCATCGT-3'; SEQ ID NO: 10) and hMIF-3' primer (5'-GCCTCGAGTTAGGCGAAG-GTGGAGTTGT-3'; SEQ ID NO: 11) by PCR.

After the amplified MIFcDHA was cleaved with EcoRI and XhoI, the digestion product was inserted between the EcoRI and XhoI sites of T7 promoter expression plasmid pET32a(+) (Novagen) to give pET32a/hMIF vector. Next, pET32a/hMIF was cleaved with NdeI and then religated thereby to remove the sequence encoding thioredoxin. This vector was cleaved with EcoRI and NspV, the cleavage site was blunt ended and then religated to give (His-hMIF) expression vector pET32a-His-hMIF of the human MIF protein added with the peptide of 30 amino acids (SEQ ID NO: 12) containing histidine tag in the N terminus of MIF.

(2) Preparation of His-hMIF Protein

After pET32a-His-hMIF was transfected to *Escherichia coli* BL21 (DE3), the cells were inoculated on ampicillin-supplemented LB medium (1% tryptone, 0.5% yeast extract, 0.5% NaCl) (LBamp medium), followed by shake culture at 37° C. overnight. The cells were transferred to LBamp medium at a density of 1% and shake-cultured at 37° C. for about 2.5 hours. Then 0.4 mM IPTG was added thereto and cultured at 15° C. for further 5 hours. After completion of the incubation, *Escherichia coli* was recovered and suspended in a binding buffer (20 mM Tris-HCl; pH 7.9, 500 mM NaCl, 5 mM imidazole) supplemented with 0.1% NP-40, followed by ultrasonication. The cell lysate was centrifuged at 4° C. and 12,000 g for 20 minutes to recover the supernatant. The recovered supernatant was filtered through a filter of 0.22 μm. Next, His Bind resin (Novagen) was charged with charge buffer (50 mM $NiSO_4$) in a 5-fold volume of the column size and then equilibrated with a binding buffer in a 3-fold volume, through which the cell lysate described above was passed to bind His-hMIF to the column and then washed with binding buffer in a 10-fold volume of the column size and wash buffer (20 mM Tris-HCl, pH 7.9, 500 mM NaCl, 60 mM imidazole) in a 6-fold volume of the column size to remove non-specifically bound proteins and accompanied substances. Next, the His-hMIF protein was eluted with elution buffer (20 mM Tris-HCl, pH 7.9, 500 mM NaCl, 1M imidazole) in a 6-fold volume. The His-hMIF obtained was dialyzed by 20 mM sodium phosphate buffer (pH 7.2) supplemented with 8M urea and 5 mM DTT, dialyzed by 5 mM DTT-containing 20 mM sodium phosphate buffer (pH 7.2), and further dialyzed with 20 mM sodium phosphate buffer (pH 7.2) alone.

Experiment 1(1)

Binding of rat MIF to N-(6-aminohexyl)-6-(4-oxo-4H-1,3-benzothiazin-2-yl)-2-pyridinecarboxamide or its hydrochloride (hereinafter briefly referred to as Compound A)

The binding of rat MIF obtained in REFERENCE EXAMPLE 2 to Compound A (cf., EXAMPLE 107 of WO 03/020719; see the formula below) was analyzed by BIA-CORE 3000 (manufactured by Biacore Co., Ltd.).

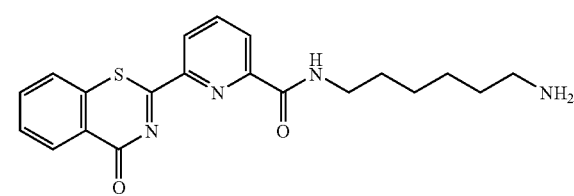

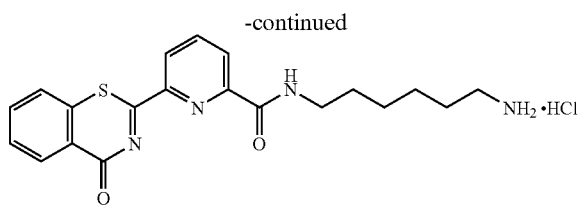

After Compound A was immobilized onto a sensor chip CM5 (manufactured by Biacore Co., Ltd.), phosphate buffered saline containing 0.005% Tween 20 containing 1 μg/ml of rat MIF was passed over the chip to assess changes in surface plasmon resonance signal as the binding of the compound to rat MIF.

The results are shown in FIG. 1.

The results reveal that Compound A strongly binds to rat MIF.

Experiment 1(2)

Binding of rat MIF to N-(6-aminohexyl)-6-(8-methyl-4-oxo-4H-1,3-benzothiazin-2-yl)pyridine-2 carboxamide or its hydrochloride (hereinafter briefly referred to as Compound C)

The binding of rat MIF obtained in REFERENCE EXAMPLE 2 to Compound C (see the formula below) was analyzed by BIACORE 3000 (manufactured by Biacore Co., Ltd.). In a manner similar to EXPERIMENT 1(1), Compound C was immobilized onto a sensor chip CM5 (manufactured by Biacore Co., Ltd.) and then, phosphate buffered saline containing 0.005% Tween 20 containing 1 μg/ml of rat MIF was passed over the chip to assess changes in surface plasmon resonance signal as the binding of the compound to rat MIF.

Figure 4:
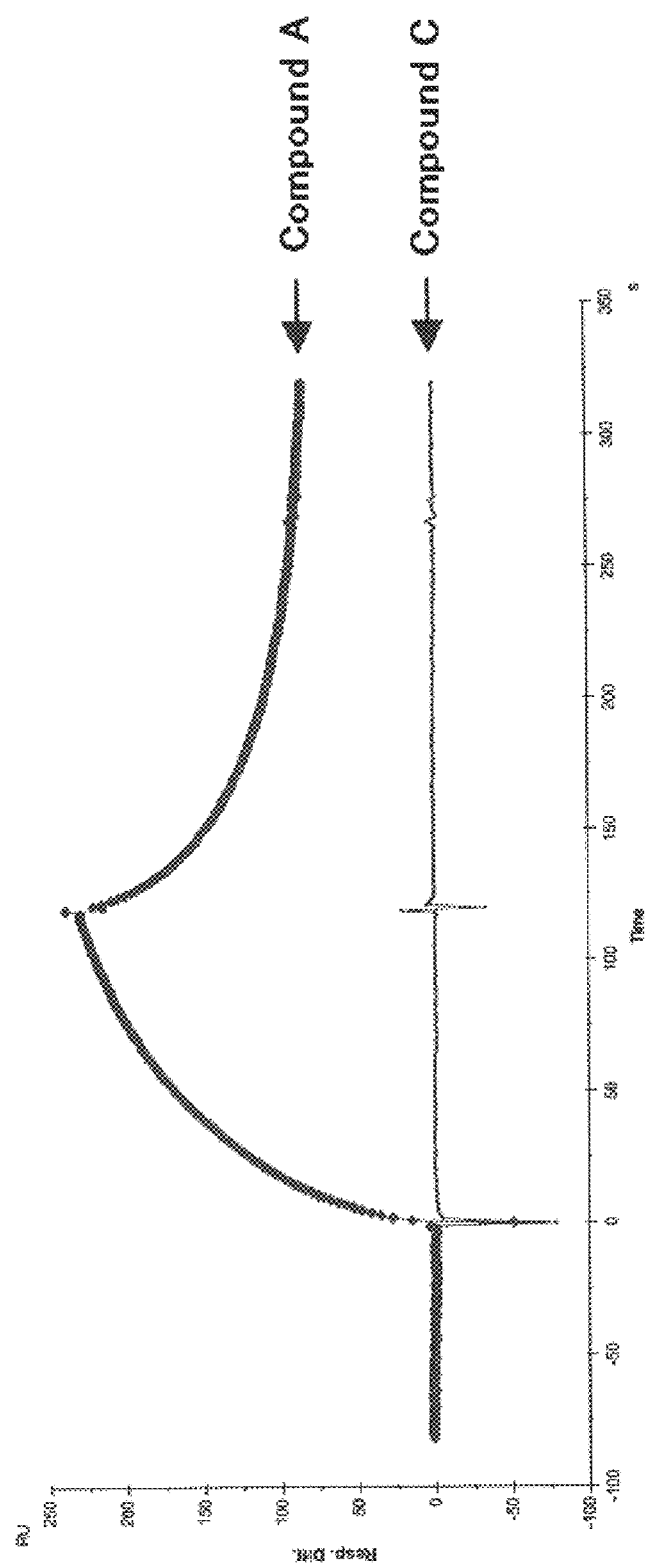
FIG. 4 shows the results of binding between rat MIF and Compound A or Compound C, wherein the ordinate represents the surface plasmon resonance signals (resonance units) and the abscissa represents time (seconds).

The results are shown in FIG. 4.

The results reveal that the binding activity of Compound C to rat MIF is weaker than that of Compound A, suggesting that the 8-position of the 1,3-benzothiazinone derivative is important for the binding to MIF.

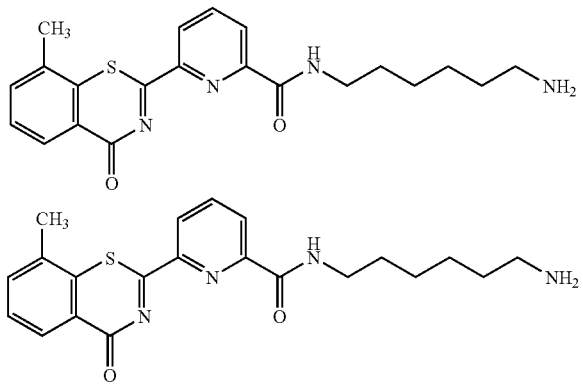

Experiment 2

Binding of MIF or Modified MIF to Compound A

The binding of human MIF (hMIF) and modified human MIF (hMIF-P1S) obtained in REFERENCE EXAMPLE 1 to Compound A was analyzed by BIACORE 3000 (manufactured by Biacore Co., Ltd.).

After Compound A was immobilized onto a sensor chip CM5 (manufactured by Biacore Co., Ltd.), HBS-EP buffer (manufactured by Biacore Co., Ltd.) containing 10 μg/ml of hMIF or hMIF-P1S was passed over the chip to assess changes in surface plasmon resonance signal as the binding of the compound to human MIF.

Figure 2:
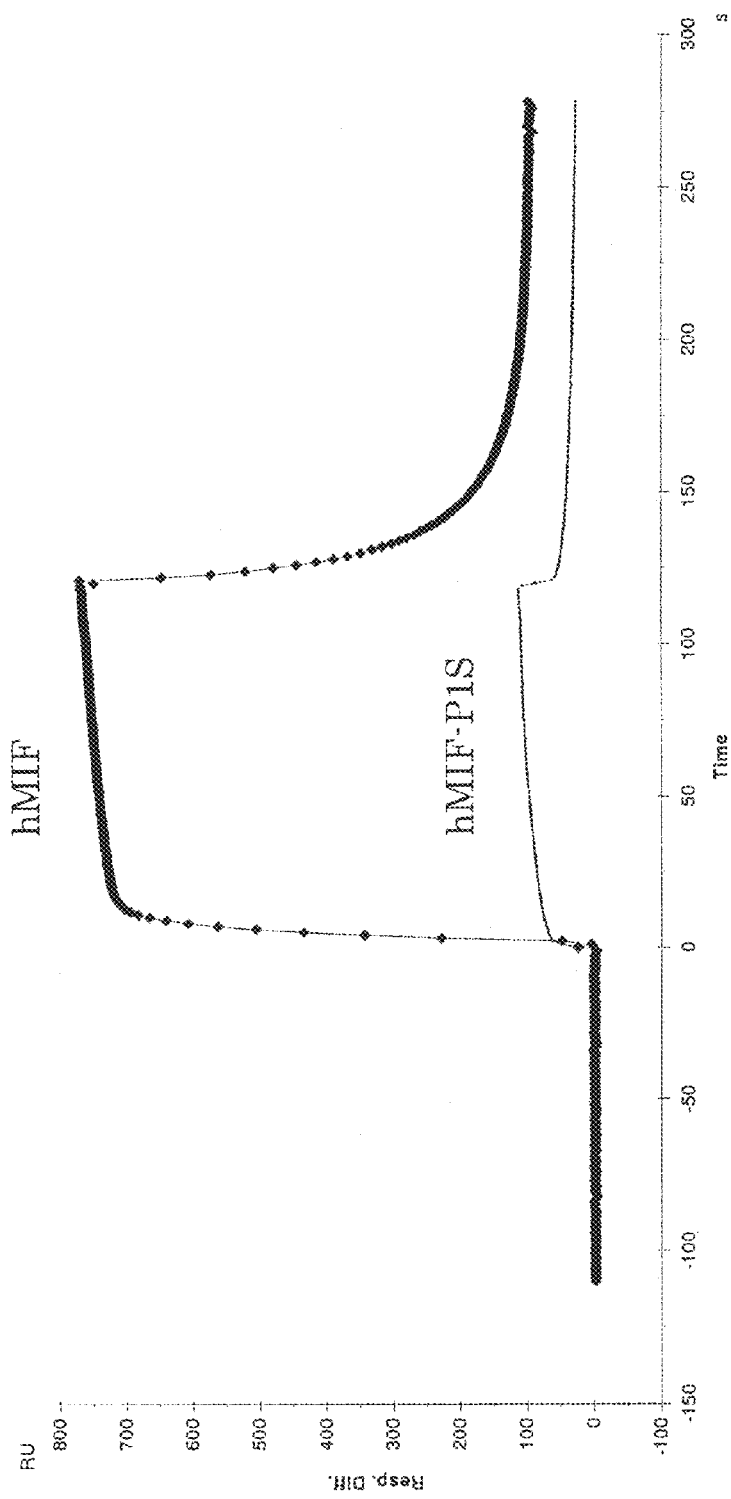
FIG. 2 shows the results of bindings between hMIF and Compound A and between hMIF-P1S and Compound A, wherein the ordinate represents the surface plasmon resonance signals (resonance units) and the abscissa represents time (seconds).

The results are shown in FIG. 2.

It is observed that the binding ability of Compound A to human MIF was greatly attenuated by introducing a variation into the N-terminal proline of human MIF. This reveals that the 1,3-benzothiazinone derivative binding specifically to MIF binds to MIF in the vicinity of its N terminus.

Figure 5:
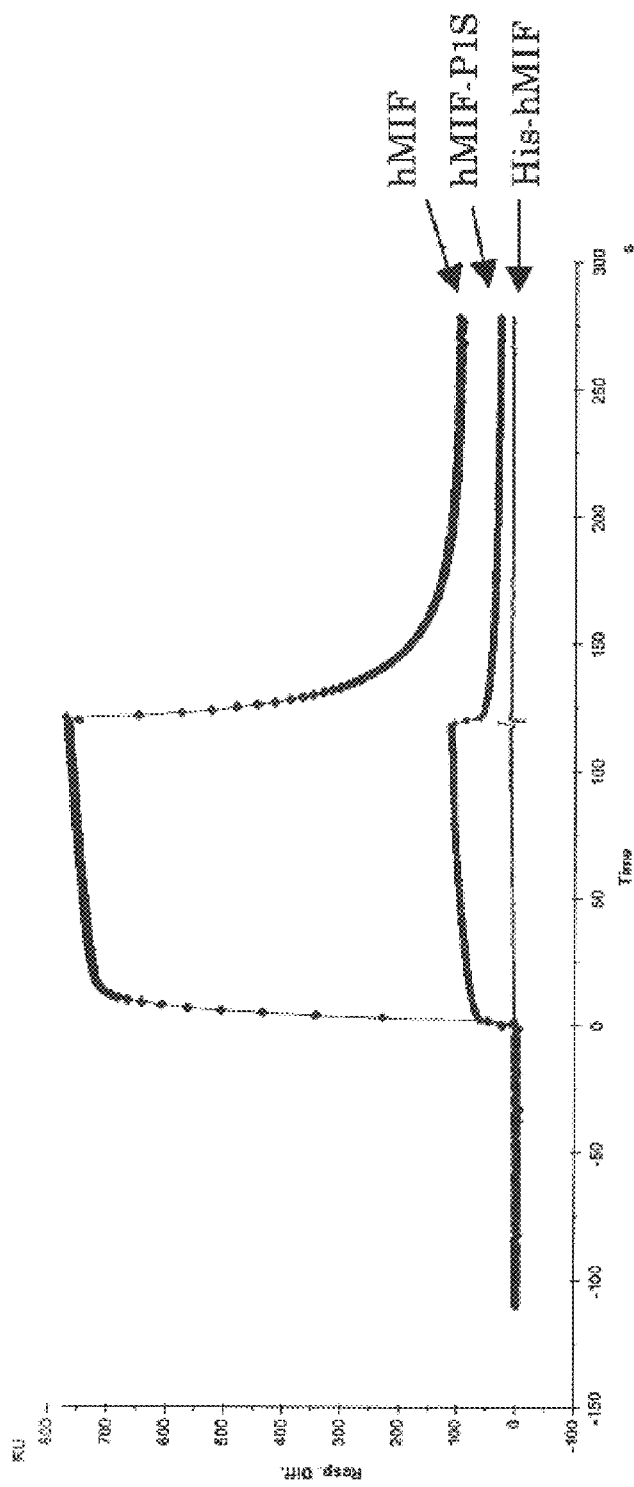
FIG. 5 shows the results of bindings between hMIF and Compound A, between hMIF-P1S and Compound A and between His-hMIF and Compound A, wherein the ordinate represents the surface plasmon resonance signals (resonance units) and the abscissa represents time (seconds).

Similarly, the binding of Compound A to His-hMIF added with the peptide to its N terminus, obtained in REFERENCE EXAMPLE 3, was analyzed. The results are shown in FIG. 5.

It is observed that the binding ability of Compound A to human MIF was greatly attenuated by adding the 30 amino acid-polypeptide containing histidine tag to the N-terminal proline of human MIF. This suggests that the N-terminal proline being free is suitable for the binding of MIF to the 1,3-benzothiazinone derivative.

Experiment 3

ARE activation activity of MIF in the presence of 2-(2-pyridyl)-4H-1,3-benzothiazin-4-one (hereinafter briefly referred to as Compound B)

After rat MIF (rMIF) obtained in REFERENCE EXAMPLE 2 was further purified by filtering through Superdex 75 (Amersham Bioscience Corp.) using AKTA Purifier (Amersham Bioscience Corp.), endotoxin was removed using Detoxi-Gel (Pierce Chemical Co.). Next, it was examined if the purified MIF showed the ARE activation activity in the presence of Compound B which binds to MIF (cf., WO 02/18356, REFERENCE EXAMPLE 1; see the formula below).

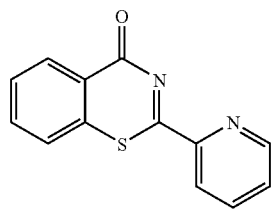 [SMILES: O=c1nc(-c2ccccn2)sc2ccccc12]

Rat H9c2 cells were suspended in Dulbecco's Modified Eagle Medium containing 10% heat-inactivated fetal calf serum (10% FEBS, D-MEM medium) at $7 \times 10^4$/ml, followed by incubation at 37° C. for about 16 hours under 5% $CO_2$. Using FuGENE6 Transfection reagent (manufactured by Roche Inc.), pGL3-Promoter Vector (manufactured by Promega) in which ARE (SEQ ID NO: 6) of rat glutathione S-transferase Ya subunit gene was integrated was transfected to the cells, followed by further incubation for about 7 hours. After completion of the incubation, the cells were recovered and suspended in 10% FBS-containing D-MEM at $1 \times 10^5$/ml, and 100 μl each of the cells were plated on each well of a 96-well opaque plate (manufactured by Falcon), followed by incubation at 37° C. for about 17 hours under 5% $CO_2$. Next, the medium was exchanged with 0.3% FBS-containing D-MEM. After the incubation was continued for a day, the medium was again exchanged with 0.3% FBS-containing D-MEM, followed by incubation at 37° C. for about 5 hours under 5% $CO_2$. Compound B and rat MIF were added to the medium, which was then incubated at 37° C. for about 24 hours under 5% $CO_2$. After completion of the incubation, 80 µl each of Steady-Glo Reagent (manufactured by Promega) was added to each well and allowed to stand at room temperature for 40 minutes. Thereafter the luminescence levels emitted by luciferase were assayed using WALLAC ARVO SX (manufactured by Perkin Elmer).

Figure 3:
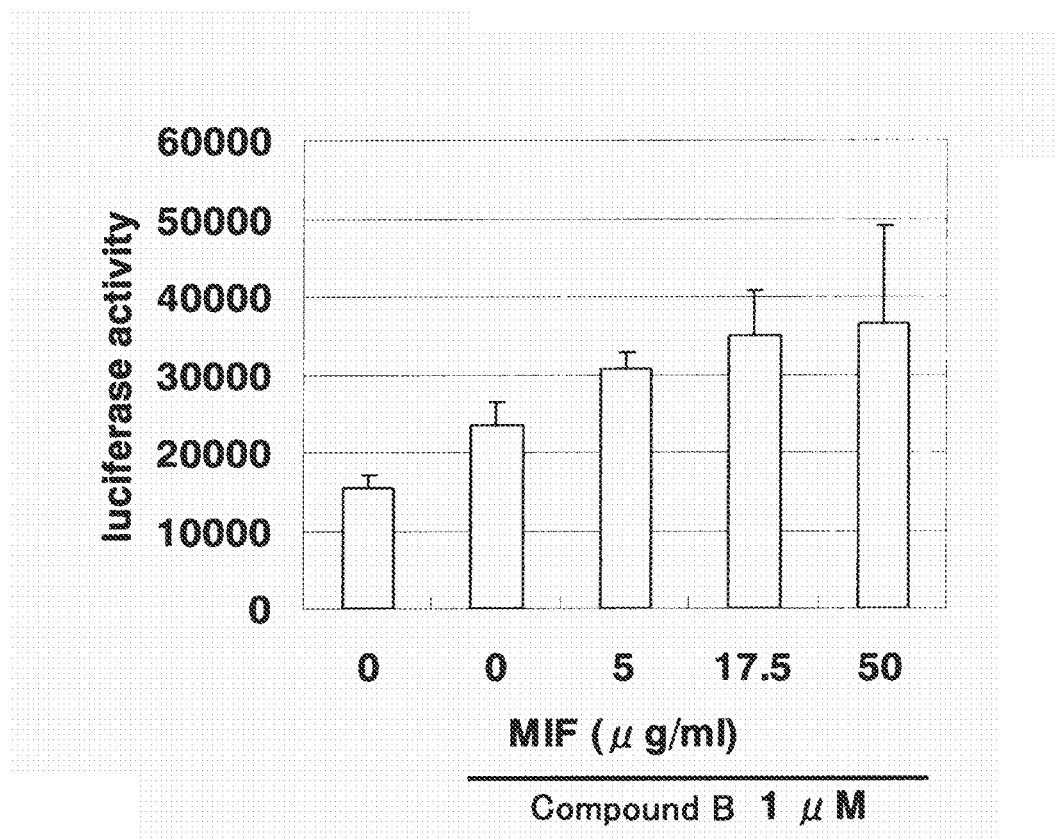
FIG. 3 shows the results of the ARE activation activity of rat MIF in the presence of Compound B, wherein the ordinate represents the luciferase luminescence level and the abscissa represents the amounts of rat MIF and Compound B (concentrations in culture medium).

The results are shown in FIG. 3. The results reveal that rat MIF showed the ARE activation activity dose-dependently in the presence of Compound B (1 µM).

Experiment 4

Induction of Expression of GST Ya (Glutathione S-Transferase Ya Subunit) and HO-1 (Heme Oxygenase-1) Genes by MIF Neonates (within one day after birth) were obtained from pregnant Wistar rats purchased from Charles River Japan, Inc. and anesthetized with ether. After sterilization with 70% ethanol, the heart was removed with forceps. After washing with phosphate buffered saline (manufactured by Takara Co., Ltd., T900), the heart removed was minced with surgical scissors. The tissue pieces were washed 4 or 5 times with phosphate buffered saline to remove most of non-cardiomyocytes derived from blood. To the tissue pieces corresponding to 10 neonates, 5 ml of an enzyme solution [a solution of trypsin (1.25 mg) (manufactured by Difco) and collagenase (0.25 mg) (manufactured by Sigma) in phosphate buffer (PBS) (1 ml)] was added. The mixture was stirred for 15 minutes with a stirrer while maintaining at 37° C.

After 2.5 ml of the enzyme solution was replenished, the mixture was stirred for further 15 minutes, and this procedure was repeated twice. Subsequently, 5 ml of Medium 199 (manufactured by Gibco) containing 10% fetal calf serum (manufactured by Biowicker, Inc.) was added to the mixture to terminate the enzymatic reaction. After filtering through a cell strainer (manufactured by Falcon), the mixture was centrifuged at 400×g for 5 minutes to collect the cells. The thus collected cells corresponding to 10 neonates were suspended in 50 ml of Medium 199 containing 10% fetal calf serum, and 10 ml each of the suspension was seeded on a 100 mm Petri dish (manufactured by Iwaki Co., Ltd.), followed by incubation for an hour in a $CO_2$ incubator set at 37° C. and 5% $CO_2$. Thereafter, the non-adherent cells were filtered through a cell strainer and then centrifuged at 400×g for 5 minutes to collect the cells. Next, the collected cells were suspended in 2 ml of a hypotonic solution [solution obtained by dissolving $NH_4Cl$ (8.29 g), $KHCO_3$ (1.0 g) and EDTA/2Na (ethylenediaminetetraacetic acid disodium; manufactured by Dojin Chemical Research Laboratories) (37 mg) in water (1 L)]. The suspension was allowed to stand for 3 minutes to disrupt erythrocytes. After 10 ml of Medium 199 containing 10% fetal calf serum was added to the suspension, the mixture was centrifuged at 400×g for 5 minutes and the collected cells were used as cardiomyocytes.

After the thus prepared cardiomyocytes derived from rat neonates were suspended in Medium 199 containing 10% fetal calf serum in $3\times10^5$ cells/ml, the suspension was plated on a 48-well plate in 0.5 ml/well, followed by incubation for a day in a $CO_2$ incubator set at 37° C. and 5% $CO_2$. After stirring with a micromixer (manufactured by Taiyo Kagaku Kogyo Co., Ltd.), the medium was replaced 3 times with serum-free Medium 199 to remove serum and rat MIF was added thereto. After incubation for further an hour, 10 µM NOR3 ((±)-(E)-4-ethyl-2-[(E)-hydroximino]-5-nitro-3-hexenamide; manufactured by Dojin Chemical Research Laboratories) was added thereto. Incubation was continued for further 3 or 6 hours. The rat MIF used was the one obtained by gel-filtering the rat MIF obtained in REFERENCE EXAMPLE 2 through Superdex 75 (manufactured by Amersham Bioscience) using AKTA purifier (manufactured by Amersham Bioscience) and then removing endotoxin by Detoxi-Gel (Pierce Chemical Co.).

After completion of the incubation, RNA was purified using RNeasy 96 kit (manufactured by Qiagen) and the mRNA levels in HO-1 and GST Ya were quantified by a Real-Time PCR System (manufactured by Applied Biosystems) using the primers and probes described below.

GST Ya (SEQ ID NO: 13)
(1) rGSTYaF1  TGCCAGCCTTCTGACCTCTTT (SEQ ID NO: 14)
(2) rGSTYaR1  CTGCAGGAACTTCTTCACATTGG

[SEQ ID NO: 15]
(3) rGSTYa-1  FAM-AAGGCCTTCAAGAGCAGAATCAGCAGC-TAMRA

GAPDH (SEQ ID NO: 16)
(1) rGAPDHF2  TGCCAAGTATGATGACATCAAGAAG (SEQ ID NO: 17)
(2) rGAPDHR2  AGCCCAGGATGCCCTTTAGT

[SEQ ID NO: 18]
(3) rGAPDH-2  VIC-TGGTGAAGCAGGCGGCCGAG-TAMRA

HO-1

(SEQ ID NO: 19)
(1) rHO-1F2  CCGCCTTCCTGCTCAACA (SEQ ID NO: 20)
(2) rHO-1R2  AAGAAACTCTGTCTGTGAGGGACTCT (SEQ ID NO: 21)
(3) rHO-1-2  FAM-CAGGCACTGCTGACAGAGGAACACAAAG-TAMRA

HO-1 mRNA and GST Ya mRNA were determined for the mRNA, 4 hours after and 7 hours after the addition of MIF, respectively, using the recovered mRNA.

Figure 6:
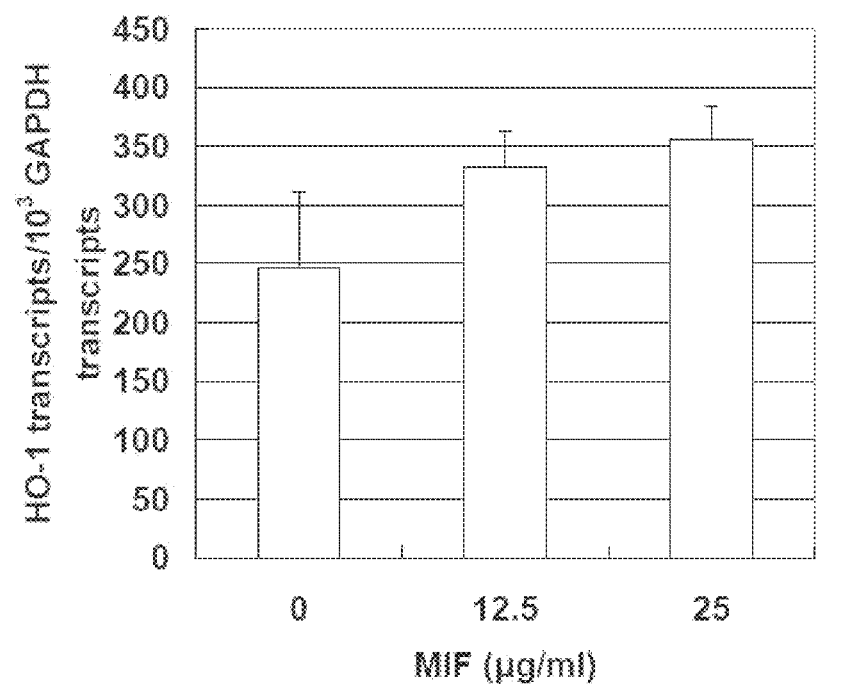
FIG. 6 shows GST Ya or HO-1 expression inducing action of rat MIF, wherein the ordinate represents the mRNA level of GST Ya or HO-1 and the abscissa represents the level of rat MIF (concentration in culture medium).
Figure 6:
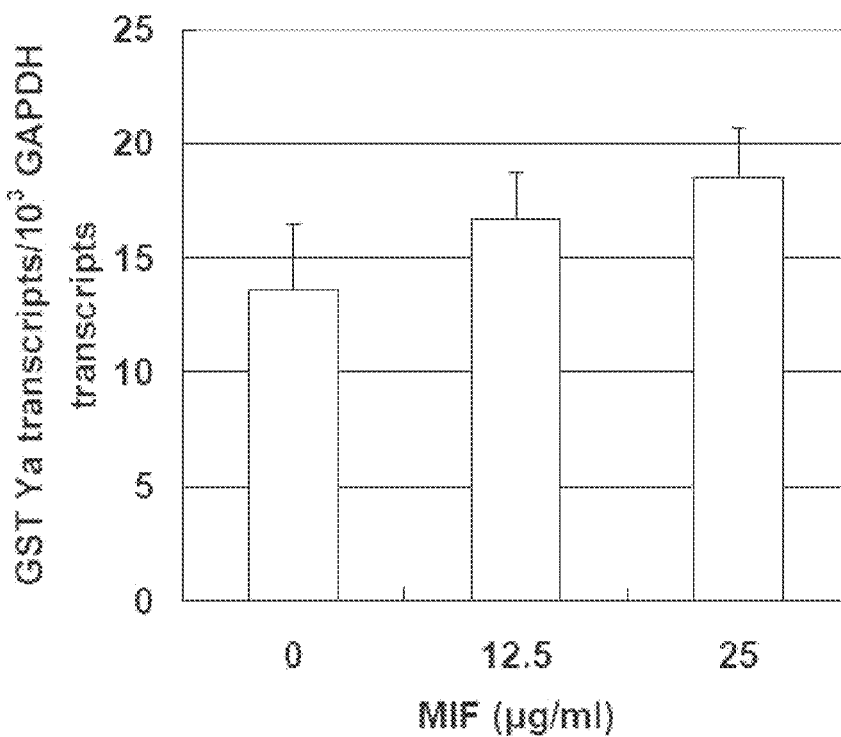

The results are shown in FIG. 6. The results reveal that MIF upregulated the expression of GST Ya and HO-1, which expression was regulated by ARE.

INDUSTRIAL APPLICABILITY (a) MIF or a modified MIF as an ARE activator and (b) the combination of MIF or a modified MIF and a substance capable of binding to MIF (such as 1,3-benzothiazinone derivatives, antibody, etc.) as an ARE activator are useful as a safe and excellent cell death inhibitor, for example, as an agent for the prevention/treatment of cardiovascular diseases, bone/joint diseases, infectious diseases, inflammatory diseases, renal diseases, central nervous system diseases, cancer, diabetes, etc.

The invention claimed is:

1. An in vitro method of activating an antioxidant response element under which a gene is controlled, the gene selected from the group consisting of Heme oxygenase-1, Liver glutathione S-transferase Ya subunit, Liver glutathione S-transferase Yc subunit, Glutathione S-transferase Yb subunit, Glutathione S-transferase Yc1 subunit, Gammma-glutamylcysteine synthetase, NAD(P)H: quinone reductase, UDP-glucuronosyltransferase exon 1, Bilirubin-specific UDP-glucuronosyltransferase, NAD(P)H-menadione oxidoreductase and Glutathione S-transferase Ya subunit, which comprises contacting an effective amount of an isolated mammalian macrophage migration inhibitory factor and an effective amount of a substance capable of binding to the macrophage migration inhibitory factor with a cell, thereby inducing the expression of the gene in the cell, wherein the substance is a 1,3-benzothiazinone derivative, and wherein the cell is a cardiomyocyte.

2. The in vitro method of claim 1, wherein the 1,3-benzothiazinone derivative is a compound represented by formula:

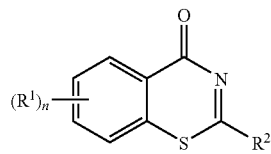

wherein $R^1$ represents hydrogen atom, a halogen atom, hydroxy, nitro, an alkyl which may optionally be halogenated, an alkoxy which may optionally be substituted, an acyl or an amino which may optionally be substituted;

$R^2$ represents a hydrocarbon group which may optionally be substituted, an aromatic heterocyclic group which may optionally be substituted, or an amino which may optionally be substituted; and, n represents 1 or 2;

or a salt thereof.

3. A method of suppressing cell death induced by oxidative stress in vitro which comprises contacting an effective amount of an isolated mammalian macrophage migration inhibitory factor thereof and an effective amount of a substance capable of binding to the isolated macrophage migration inhibitory factor with a cell, thereby suppressing cell death of the cell, wherein the substance is a 1,3-benzothiazinone derivative, and wherein the cell is a cardiomyocyte.

4. The method of claim 3, wherein the 1,3-benzothiazinone derivative is a compound represented by formula:

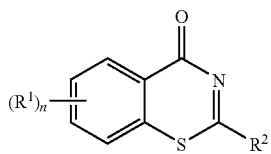

wherein $R^1$ represents hydrogen atom, a halogen atom, hydroxy, nitro, an alkyl which may optionally be halogenated, an alkoxy which may optionally be substituted, an acyl or an amino which may optionally be substituted;

$R^2$ represents a hydrocarbon group which may optionally be substituted, an aromatic heterocyclic group which may optionally be substituted, or an amino which may optionally be substituted; and, n represents 1 or 2; or a salt thereof.

5. The in vitro method of claim 1, wherein the isolated mammalian macrophage migration inhibitory factor is a protein comprising the amino acid sequence represented by SEQ ID NO: 1, or a salt thereof.

6. The method of claim 3, wherein the isolated mammalian macrophage migration inhibitory factor is a protein comprising the amino acid sequence represented by SEQ ID NO: 1, or a salt thereof.

\* \* \* \* \*